(12) United States Patent
Makino et al.

(10) Patent No.: US 10,376,926 B2
(45) Date of Patent: Aug. 13, 2019

(54) INSPECTION AND SORTING SYSTEM

(71) Applicant: ISHIDA CO., LTD., Kyoto-shi, Kyoto (JP)

(72) Inventors: Koichi Makino, Ritto (JP); Kazuyuki Sugimoto, Ritto (JP)

(73) Assignee: ISHIDA CO., LTD., Kyoto (JP)

( * ) Notice: Subject to any disclaimer, the term of this patent is extended or adjusted under 35 U.S.C. 154(b) by 96 days.

(21) Appl. No.: 15/501,967

(22) PCT Filed: Aug. 5, 2015

(86) PCT No.: PCT/JP2015/072181
§ 371 (c)(1),
(2) Date: Feb. 6, 2017

(87) PCT Pub. No.: WO2016/021623
PCT Pub. Date: Feb. 11, 2016

(65) Prior Publication Data
US 2017/0225200 A1 Aug. 10, 2017

(30) Foreign Application Priority Data
Aug. 8, 2014 (JP) .................................. 2014-163088

(51) Int. Cl.
*B07C 5/36* (2006.01)
*G01N 23/04* (2018.01)
*B07C 5/34* (2006.01)

(52) U.S. Cl.
CPC ............ *B07C 5/361* (2013.01); *B07C 5/3416* (2013.01); *B07C 5/363* (2013.01); *G01N 23/04* (2013.01);
(Continued)

(58) Field of Classification Search
CPC ....... B07C 5/361; B07C 5/3416; B07C 5/346; B07C 5/344; B07C 5/342; B07C 5/363;
(Continued)

(56) References Cited

U.S. PATENT DOCUMENTS 3,386,575 A * 6/1968 Quinn ....................... B07C 5/00
 209/526
5,353,937 A * 10/1994 Childress ................ B07C 5/342
 209/563

(Continued)

FOREIGN PATENT DOCUMENTS

DE 102006029450 A1 1/2008
EP 2163886 A1 3/2010
(Continued)

OTHER PUBLICATIONS

Extended European Search Report of the corresponding European Patent Application No. 15829654.1, dated Jun. 23, 2017.
(Continued)

*Primary Examiner* — Joseph C Rodriguez
*Assistant Examiner* — Kalyanavenkateshware Kumar
(74) *Attorney, Agent, or Firm* — Global IP Counselors, LLP

(57) ABSTRACT

An inspection and sorting system sorts conveyed articles. The system is provided with a conveyance device, an X-ray inspection device, and a sorting device. The conveyance device conveys inspection articles. The X-ray inspection device inspects the conveyed inspection articles. The sorting device has an air sorting mechanism that sorts the conveyed inspection articles in a sorting operation. The sorting device has a sorting information receiving component, a reference signal receiving component, and a sorting mechanism control component. The sorting information receiving component receives sorting information relating to the sorting of
(Continued)

the inspection articles based on an inspection result of the X-ray inspection device. The reference signal receiving component receives a fixed-interval reference signal relating to the conveyance by the conveyance device. The sorting mechanism control component controls the air sorting mechanism to execute the sorting operation based on the sorting information at a timing adjusted by the reference signal.

11 Claims, 11 Drawing Sheets

(52) U.S. Cl.
CPC .............. *G01N 2223/1016* (2013.01); *G01N 2223/3307* (2013.01); *G01N 2223/618* (2013.01); *G01N 2223/643* (2013.01); *G01N 2223/652* (2013.01)

(58) Field of Classification Search
CPC ............. G01N 23/04; G01N 2223/618; G01N 2223/643; G01N 2223/652; G01N 2223/1016; G01N 2223/3307
See application file for complete search history.

(56) References Cited

U.S. PATENT DOCUMENTS

| | | | | |
|---|---|---|---|---|
| 6,060,677 A | * | 5/2000 | Ulrichsen | B07C 5/342 209/577 |
| 6,266,390 B1 | * | 7/2001 | Sommer, Jr. | B07C 5/3427 378/45 |
| 7,763,820 B1 | * | 7/2010 | Sommer, Jr. | B07C 5/342 209/576 |
| 2010/0150308 A1 | * | 6/2010 | Tsuno | B07C 5/346 378/54 |
| 2013/0184853 A1 | * | 7/2013 | Roos | B07C 5/12 700/214 |
| 2013/0195244 A1 | * | 8/2013 | Hosokawa | G01N 23/04 378/53 |
| 2014/0294151 A1 | * | 10/2014 | Suyama | G01N 23/083 378/62 |

FOREIGN PATENT DOCUMENTS

| | | |
|---|---|---|
| GB | 2079633 A | 1/1982 |
| JP | 56-10980 U | 1/1981 |
| JP | 59-142083 U | 9/1984 |
| JP | 05-076849 A | 3/1993 |
| JP | 06-039352 A | 2/1994 |
| JP | 2002-243664 A | 8/2002 |
| JP | 2002-362729 A | 12/2002 |
| JP | 2012-193001 A | 10/2012 |
| WO | 2009-101772 A1 | 8/2009 |

OTHER PUBLICATIONS

Translation of the Written Opinion of the International Searching Authority, dated Feb. 23, 2017.

* cited by examiner

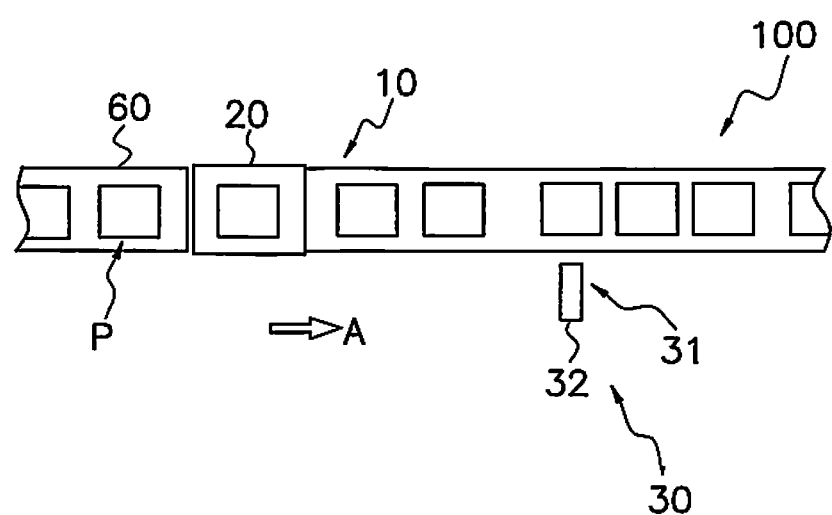
F I G. 1

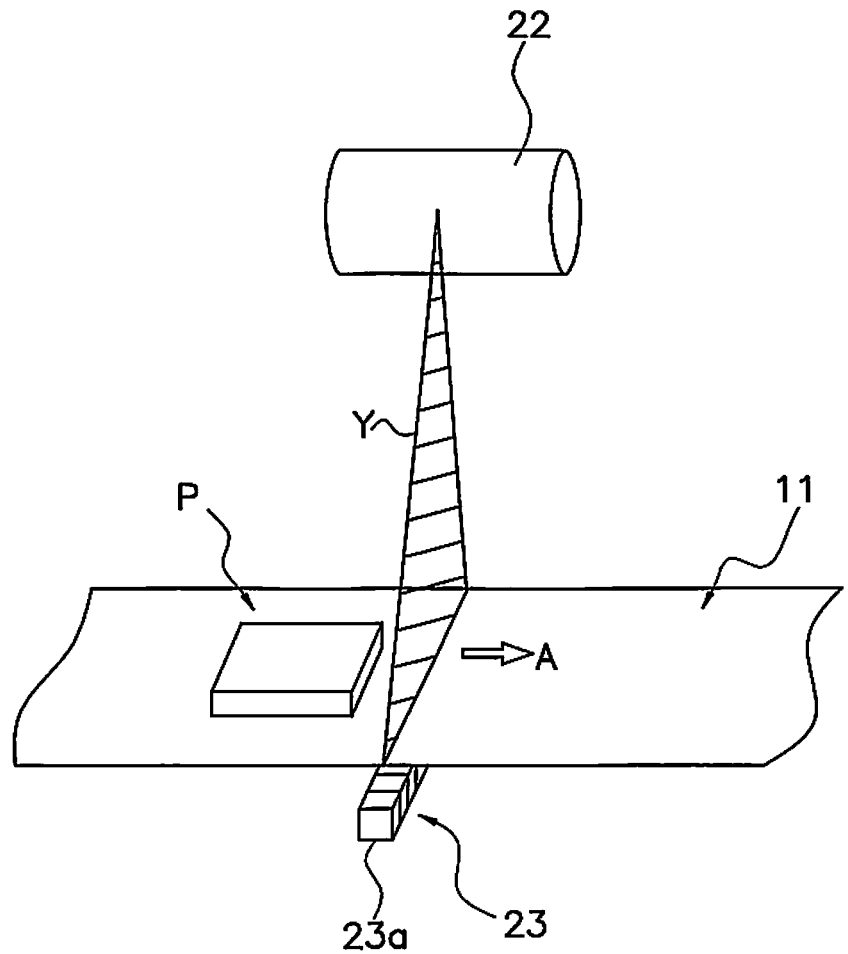
F I G. 3

INSPECTION AND SORTING SYSTEM

CROSS-REFERENCE TO RELATED APPLICATIONS

This U.S. National stage application of PCT/JP2015/072181 claims priority under 35 U.S.C. § 119(a) to Japanese Patent Application No. 2014-163088, filed in Japan on Aug. 8, 2014, the entire contents of which are hereby incorporated herein by reference.

TECHNICAL FIELD

The present invention relates to an inspection and sorting system that inspects articles and sorts the conveyed articles based on the inspection results.

BACKGROUND ART

Conventionally, inspection and sorting systems that inspect articles and sort the conveyed articles based on the inspection results have been known. For example, patent document 1 (Japanese Laid Open Publication No. 2002-362729) discloses an inspection and sorting system which, based on the results of a metal contamination inspection and a weighing inspection, blows air onto articles conveyed on a transport conveyor to thereby sort the articles.

Currently, from the standpoint of improving efficiency, it is desired that inspection and sorting systems sort conveyed articles at a high processing speed and with good precision.

SUMMARY OF INVENTION

Technical Problem

However, inspection and sorting systems have a following problem in the case that articles conveyed from an inspection device is sorted at a high processing speed based on the inspection results sent to a sorting device, The sorting device receives the inspection results from the inspection device and sorts the articles, but there are cases where, owing to the specifications or the like of the control system of the inspection device, the timing when the sorting device receives the inspection results from the inspection device varies. In such cases, when the sorting device activates a sorting mechanism based on the timing when it received the inspection results, the timing when the sorting mechanism should be activated may be out of sync with the timing when the sorting mechanism actually operates. As a result, situations may occur where articles that should be sorted are not sorted or articles that should not be sorted are sorted and the precision of the sorting is lowered.

This kind of problem can be prevented by sufficiently lengthening the time of the sorting operation of the sorting device and keeping large intervals between the conveyed articles. However, if the system is configured in this way, the number of articles to be processed per unit time is reduced.

It is an object of the present invention to provide an inspection and sorting system that can sort conveyed articles, based on the inspection results, at a high processing speed and with good precision.

Solution to Problem

An inspection and sorting system pertaining to a first aspect of the present invention is provided with a conveying means, an inspection device, and a sorting device. The conveying means is configured to convey articles. The inspection device is configured to inspect the articles conveyed by the conveying means. The sorting device has a sorting mechanism being configured to execute a sorting operation in which the articles conveyed by the conveying means are sorted. The sorting device has a first receiving component, a second receiving component, and a sorting mechanism control component. The first receiving component is configured to receive sorting information relating to the sorting of the articles based on an inspection result of the inspection device. The second receiving component is configured to receive a fixed-interval reference signal relating to the conveyance by the conveying means. The sorting mechanism control component is configured to control the sorting mechanism to execute the sorting operation based on the sorting information at a timing adjusted by the reference signal.

In the inspection and sorting system pertaining to the first aspect, the sorting mechanism executes the sorting operation based on the fixed-interval reference signal relating to the conveyance by the conveying means for adjusting the timing of the execution of the sorting operation as well as the sorting information relating to the sorting. For that reason, the sorting operation can be executed at an appropriate timing regardless of variations in the reception timing of the sorting information. As a result, the articles conveyed from the inspection device can be sorted, based on the inspection results, at a high processing speed and with good precision.

An inspection and sorting system pertaining to a second aspect of the present invention is the inspection and sorting system pertaining to the first aspect, wherein the reference signal is a signal transmitted to the second receiving component each time the conveying means conveys a first distance.

In the inspection and sorting system pertaining to the second aspect, the second receiving component receives the reference signal each time the conveying means conveys a fixed distance. The articles conveyed from the inspection device can be therefore sorted, at a high processing speed and with good precision based on a timing adjusted by the reference signal and the inspection results.

An inspection and sorting system pertaining to a third aspect of the present invention is the inspection and sorting system pertaining to the second aspect, wherein the inspection device is an X-ray inspection device having a line sensor. The line sensor is configured to image, in every single imaging, a predetermined width along a conveyance direction of the conveyance means. The first distance is an integral multiple of the predetermined width.

In the inspection and sorting system pertaining to the third aspect, the reference signal is transmitted each time the conveyance distance of the conveying means becomes equal to the integral multiple of the predetermined width for which the line sensor of the X-ray inspection device images. It is therefore easy to execute the sorting operation at an appropriate timing matching the inspection results of the X-ray inspection.

An inspection and sorting system pertaining to a fourth aspect of the present invention is the inspection and sorting system pertaining to any of the first aspect to the third aspect, wherein the inspection device is configured to inspect the non-defective/defective or rank of the articles.

Here, the articles can be sorted by the sorting device based on the non-defective/defective or rank of the articles.

An inspection and sorting system pertaining to a fifth aspect of the present invention is the inspection and sorting system pertaining to any of the first aspect to the fourth aspect, is further provided with a conveyance checking sensor and a judging component. The conveyance checking sensor is configured to detect the articles on the downstream side of the sorting mechanism in the conveyance direction of the conveying means. The judging component is configured to judge, based on the detection results of the conveyance checking sensor, success or failure of the sorting by the sorting mechanism. The judging component is configured to judge the success or failure of the sorting by the sorting mechanism based on the sorting information and in accordance with whether or not the conveyance checking sensor detects the articles at a check timing adjusted by the reference signal.

In the inspection and sorting system pertaining to the fifth aspect, the sensor which detects the articles conveyed on the downstream side of the sorting mechanism is installed and the success or failure of the sorting is judged based on the sorting information and in accordance with whether or not an article is detected at the check timing adjusted by the reference signal. That is to say, here, the presence or absence of an article is judged at an accurate check timing adjusted by the reference signal in the same way as the timing of the operation of the sorting mechanism, and the success or failure of the sorting is thereby judged. For that reason, the success or failure of the sorting can be judged at a high processing speed and accurately.

An inspection and sorting system pertaining to a sixth aspect of the present invention is the inspection and sorting system pertaining to any of the first aspect to the fifth aspect, wherein the timing is configured to determine based on a fixed delay time determined by a characteristic of the sorting mechanism.

Here, the timing of the sorting operation is determined based on the fixed delay time determined by the characteristic of the sorting mechanism. Therefore, even in a case where the conveyance speed of the conveying means is changed, the sorting operation can be executed at an appropriate timing.

Advantageous Effects of Invention

In the inspection and sorting system pertaining to the present invention, the sorting mechanism executes the sorting operation based on the fixed-interval reference signal relating to the conveyance by the conveying means for adjusting the timing of the execution of the sorting operation as well as the sorting information relating to the sorting. For that reason, the sorting operation can be executed at an appropriate timing regardless of variations in the reception timing of the sorting information. As a result, the articles conveyed from the inspection device can be sorted, based on the inspection results, at a high processing speed and with good precision.

BRIEF DESCRIPTION OF DRAWINGS

FIG. 1 is a schematic diagram of an inspection and sorting system pertaining to a first embodiment of the present invention.

FIG. 3 is a simple configuration diagram of the inside of a shield box of the X-ray inspection device of FIG. 2.

FIG. 5(*a*) is an example of unit sorting information generated by the X-ray inspection device of the inspection and sorting system of FIG. 1. FIG. 5(*b*) is a drawing showing positions of inspection articles on a conveyor which serve as the basis of the unit sorting information of FIG. 5(*a*). Inspection articles to which hatching has been added in FIG. 5(*b*) represent inspection articles contaminated with foreign matter.

DESCRIPTION OF EMBODIMENTS

Figure 2:
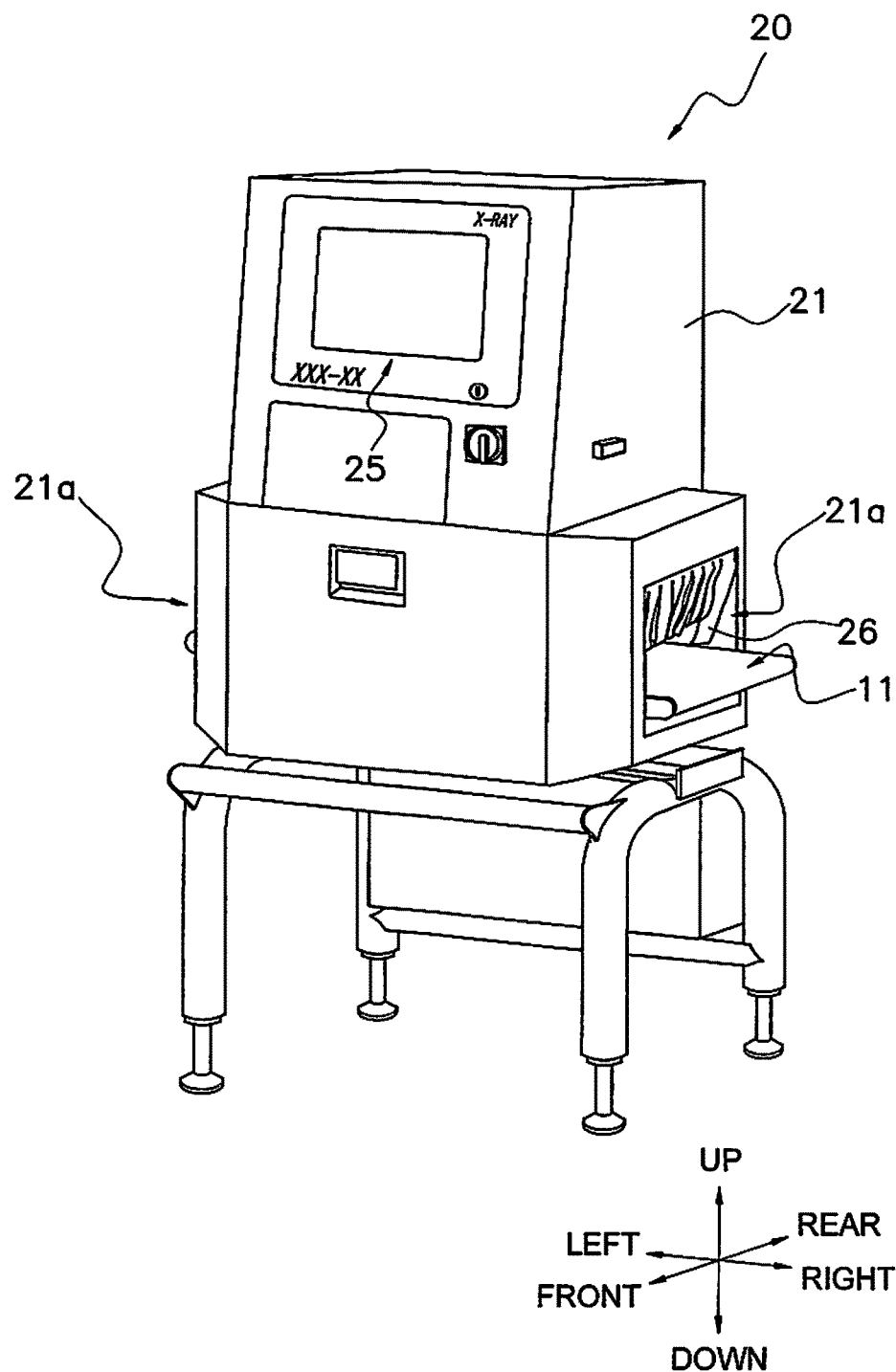
FIG. 2 is an external perspective view of an X-ray inspection device included in the inspection and sorting system of FIG. 1.

Embodiments of an inspection and sorting system pertaining to the present invention will be described below with reference to the drawings. It should be noted that the following embodiments are merely specific examples and can be appropriately changed without departing from the scope of the present invention.

First Embodiment

An inspection and sorting system 100 pertaining to a first embodiment of the present invention will be described.

(1) Overall Configuration

The inspection and sorting system 100 pertaining to the first embodiment is a system that inspects inspection articles P (also referred to as articles or articles to be inspected), such as food articles, being conveyed and sorts the inspection articles P based on the inspection results. Specifically, the inspection and sorting system 100 sorts the inspection articles P so that non-defective articles not contaminated with foreign matter is conveyed to a downstream process (e.g., a boxing process) and defective articles contaminated with foreign matter is removed from the line based on the results of a foreign matter inspection of the inspection articles P.

The inspection and sorting system 100 is mainly provided with a conveyance device 10, an X-ray inspection device 20, and a sorting device 30 (see FIG. 1).

The conveyance device 10 receives the inspection articles P conveyed thereto by an upstream conveyor unit 60 and conveys the received inspection articles P. The arrow A in FIG. 1 indicates the conveyance direction of the conveyance device 10. The X-ray inspection device 20 performs a foreign matter inspection of the inspection articles P conveyed by the conveyance device 10. The sorting device 30 executes a sorting operation that sorts the inspection articles P conveyed by the conveyance device 10, based on the inspection results of the X-ray inspection device 20.

(2) Detailed Configuration

The conveyance device 10, the X-ray inspection device 20, and the sorting device 30 of the inspection and sorting system 100 will be described below in detail.

(2-1) Conveyance Device

The conveyance device 10 (also referred to as a conveying device) is an example of conveying means that conveys the inspection articles P. The conveyance device 10 receives the inspection articles P conveyed thereto by the upstream conveyor unit 60 and conveys the inspection articles P in such a way that the inspection articles P pass through a later-described shield box 21 of the X-ray inspection device 20. Furthermore, the conveyance device 10 conveys the inspection articles P that have passed through the shield box 21 to the sorting device 30 on the downstream side of the X-ray inspection device 20. More specifically, the conveyance device 10 conveys the inspection articles P that have passed through the shield box 21 so that those inspection articles P pass through the neighborhood of an air sorting mechanism 31 of the sorting device 30 described later. Moreover, the conveyance device 10 conveys inspection articles P that are not sorted by the air sorting mechanism 31 of the sorting device 30 (inspection articles P being judged to be non-defective articles as a result of the inspection) further downstream.

Figure 4:
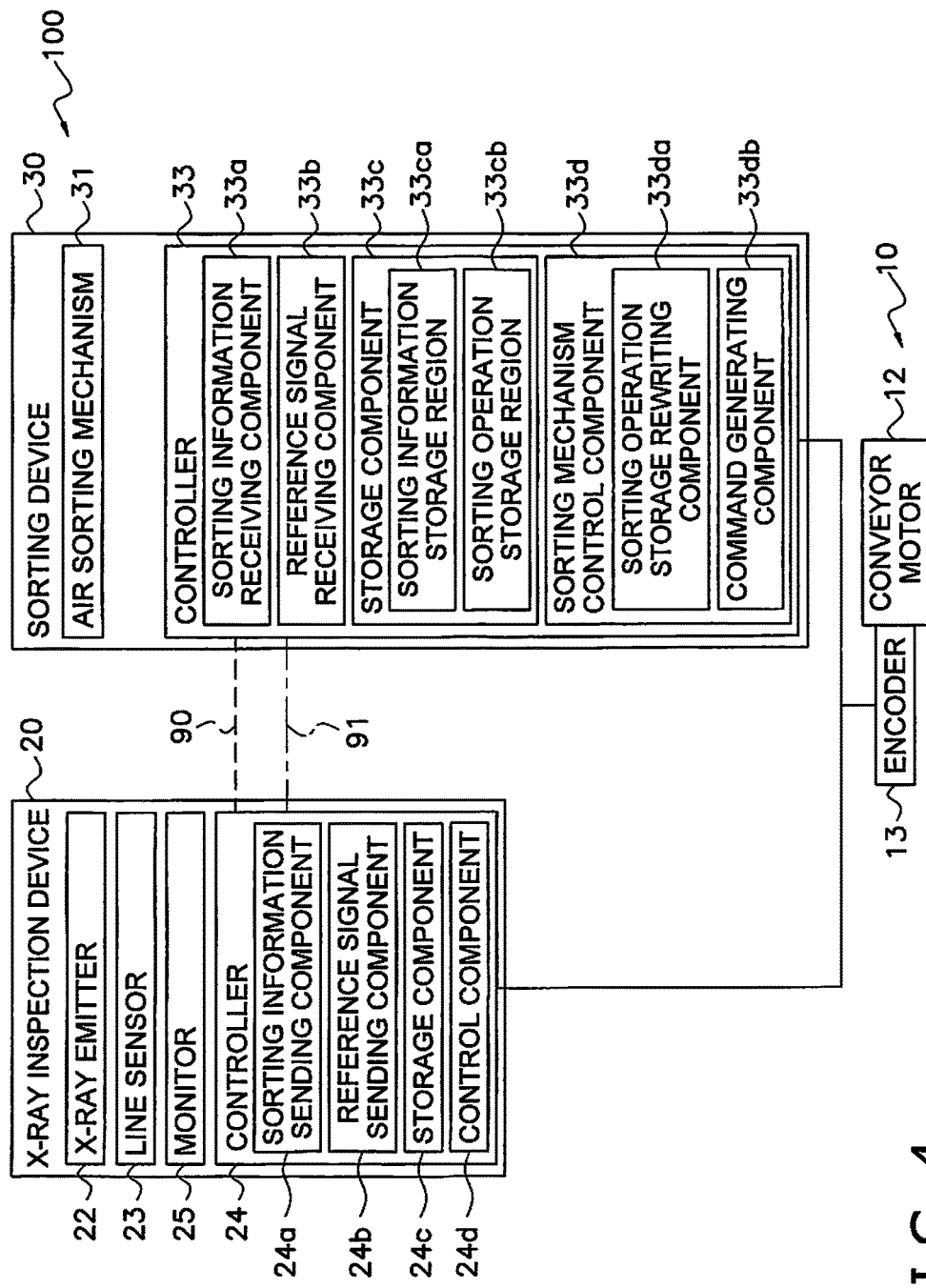
FIG. 4 is a block diagram of the inspection and sorting system of FIG. 1.

The conveyance device 10 mainly has an endless conveyor belt 11 (see FIG. 3), a drive roller (not shown in the drawings), and a conveyor motor 12 (see FIG. 4). Since drive rollers for endless conveyor belts are convention mechanical devices, further description is omitted for the sake of brevity.

The drive roller (not shown in the drawings) is driven by the conveyor motor 12. When the drive roller is driven, the conveyor belt 11 rotates so that the inspection articles P placed on the conveyor belt 11 are conveyed.

The conveyor motor 12 is an inverter-controllable motor. Since inverter-controllable motors are conventional electromechanical devices well known in the art, further description is omitted for the sake of brevity. The conveyor motor 12 is inverter-controlled by a command from a controller 24 of the X-ray inspection device 20 described later, so that the rotational speed of the drive roller is adjusted. As a result, the conveyance speed of the inspection articles P placed on the conveyor belt 11 is finely and precisely controlled for synchronized movement control with operation of the sorting device 30, as described further below. An encoder 13 is attached to the conveyor motor 12. The encoder 13 detects the conveyance distance and conveyance speed of the inspection articles P by the conveyance device 10 and sends them to the controller 24 of the X-ray inspection device 20 and a controller 33 of the sorting device 30 (see FIG. 4).

It should be noted that the conveyance device 10 may have one conveyor belt 11, one drive roller, and one conveyor motor 12, or may have a plurality of conveyor belts 11, and/or a plurality of drive rollers, and/or a plurality of conveyor motors 12.

(2-2) X-Ray Inspection Device

The X-ray inspection device 20 is an example of an inspection device that inspects the inspection articles P conveyed by the conveyance device 10. The X-ray inspection device 20 irradiates X-ray to the inspection articles P continuously conveyed by the conveyance device 10 to perform an inspection as to whether or not the inspection articles P are contaminated with foreign matter based on the amount of X-ray that has transmitted through the inspection articles P.

The X-ray inspection device 20 mainly has the shield box 21 (see FIG. 2), an X-ray emitter 22 (see FIG. 3), a line sensor 23 (see FIG. 3), a monitor 25 having a touch panel function (see FIG. 2), and the controller 24 (see FIG. 4).

Each configuration of the X-ray inspection device 20 will be described below. It should be noted that when describing positional relationships or the like in the description of the X-ray inspection device 20 below, the expressions such as "front (front face)," "rear (back face)," "left," "right," "upper," and "lower" may be used, and unless otherwise specified these express "front (front face)," "rear (back face)," "left," "right," "upper," and "lower" in accordance with the arrows in FIG. 2.

(2-2-1) Shield Box

The shield box 21 is a casing that accommodates the X-ray emitter 22, the line sensor 23, the controller 24, and the like. Furthermore, the monitor 25, a key insertion opening, a power switch, and the like are disposed in the upper front portion of the shield box 21 (see FIG. 2). Openings 21a are formed in the left and right side faces of the shield box 21 (see FIG. 2).

The conveyor belt 11 of the conveyance device 10 is disposed inside the shield box 21. Specifically, the conveyor belt 11 is disposed through the openings 21a formed in both side faces of the shield box 21. The opening 21a on the upstream side in the conveyance direction of the conveyor belt 11 functions as an inlet through which the inspection articles P conveyed by the conveyor belt 11 are conveyed into the shield box 21. The opening 21a on the downstream side in the conveyance direction of the conveyor belt 11 functions as an outlet through which the inspection articles P conveyed by the conveyor belt 11 are conveyed out from the shield box 21. It should be noted that the openings 21a are closed off by shield curtains 26 in order to prevent leakage of X-ray to the outside of the shield box 21 (see FIG. 2). The shield curtains 26 are made of rubber including lead, tungsten, or the like. The shield curtains 26 are pushed out of the way by the inspection articles P when the inspection articles P are conveyed in and out through the openings 21a.

(2-2-2) X-Ray Emitter

The X-ray emitter 22 is disposed above the conveyor belt 11 inside the shield box 21 (see FIG. 3). The X-ray emitter 22 emits X-ray, in a fan-shaped emission range Y (see the section with the hatching in FIG. 3), toward the line sensor 23 disposed under the conveyance surface of the conveyor belt 11. The emission range Y of the X-ray radiation of the X-ray emitter 22 extends orthogonally to the conveyance surface of the inspection articles P of the conveyor belt 11. Furthermore, the emission range Y spreads in a fan shape in a direction intersecting the conveyance direction (see the arrow A in FIG. 3) of the conveyor belt 11. In other words, the X-ray radiation emitted from the X-ray emitter 22 spreads in the width direction of the conveyor belt 11.

(2-2-3) Line Sensor

The line sensor 23 is disposed below the conveyance surface of the conveyor belt 11 and detects the X-ray transmitted through the inspection articles P and/or the conveyor belt 11. The line sensor 23 mainly has numerous X-ray detection elements 23a. The X-ray detection elements 23a are horizontally disposed in a straight line orthogonal to the conveyance direction (see the arrow A in FIG. 3) of the conveyor belt 11 or in other words along the width direction of the conveyor belt 11 (see FIG. 3).

Each X-ray detection element 23a detects the X-ray transmitted through the inspection articles P and/or the conveyor belt 11 and outputs an X-ray transmission signal based on the detected X-ray transmission amount (X-ray intensity). The X-ray transmission signals are sent to the controller 24 and used for creating X-ray images of the inspection articles P. The controller 24 performs a foreign matter contamination inspection of the inspection articles P based on the X-ray images created on the basis of the X-ray transmission signals or in other words created on the basis of the X-ray transmission amounts.

Furthermore, the line sensor 23 also functions as a sensor for detecting the timing when the inspection article P passes through the fan-shaped X-ray emission range Y (see FIG. 3). Specifically, when the inspection article P conveyed by the conveyor belt 11 reaches the position above the line sensor 23 (the emission range Y), the line sensor 23 outputs an X-ray transmission signal (a first signal) representing a voltage equal to or less than a predetermined threshold value. On the other hand, in a case where the inspection article P is not passing through the emission range Y, the line sensor 23 outputs an X-ray transmission signal (a second signal) representing a voltage exceeding the predetermined threshold value. The first signal and the second signal are input to the controller 24 to thereby detect the presence or absence of the inspection article P in the emission range Y. It should be noted that the predetermined threshold value is a value set arbitrarily in order to determine the presence or absence of the inspection article P.

(2-2-4) Monitor

The monitor 25 is a liquid crystal display. The monitor 25 displays the X-ray images of the inspection articles P, the inspection results of the inspection articles P, and the like. The monitor 25 also has a touch panel function and receives the input of inspection parameters and so forth by an operator.

(2-2-5) Controller

The controller 24 is a computer that controls each part of the X-ray inspection device 20. The controller 24 mainly has a central processing unit (CPU) that performs calculation and control, a read-only memory (ROM), a random access memory (RAM), a hard disk, and the like that serve as storage components storing information. The controller 24 preferably includes a microcomputer with an inspection device and article sorting control program that controls the various components of the inspection and sorting system 100 as discussed herein. The controller 24 can also include other conventional components such as an input interface circuit and an output interface circuit. The memory circuit stores processing results and control programs such as ones for conveyance, sorting and X-ray operations that are run by a processor circuit of the system. The controller 24 is operatively coupled to the inspection and sorting system 100 in a conventional manner. The internal RAM of the controller 24 stores statuses of operational flags and various control data. The controller 24 is capable of and configured to selectively control any of the components of the control system. It will be apparent to those skilled in the art from this disclosure that the precise structure and algorithms for the controller 24 can be any combination of hardware and software that carries out the functions of the present invention.

The controller 24 has a sorting information sending component 24a and a reference signal sending component 24b that send information/signals to the controller 33 of the sorting device 30 described later (see FIG. 4). Furthermore, the controller 24 has a storage component 24c and a control component 24d (see FIG. 4). The control component 24d mainly has a CPU and executes a program stored in the storage component 24c to thereby generate the X-ray images and determine, based on the generated X-ray images, whether or not the inspection articles P are contaminated with foreign matter. Furthermore, the control component 24d controls the operation of each part of the X-ray inspection device 20, such as the X-ray emitter 22 and the line sensor 23. The various inspection parameters used in the foreign matter inspection, the results of the foreign matter inspection of the inspection articles P, and later-described unit sorting information d generated by the control component 24d are stored in the storage component 24c.

The controller 24 is electrically connected to the X-ray emitter 22, the line sensor 23, and the monitor 25. Furthermore, the controller 24 is also electrically connected to the conveyor motor 12 and the encoder 13 of the conveyance device 10 (see FIG. 4). The controller 24 acquires data relating to the rotation speed of the conveyor motor 12 from the encoder 13 and grasps, based on the acquired data, the conveyance distance and conveyance speed of the inspection articles P.

Furthermore, the controller 24 is connected to the controller 33 of the sorting device 30 by a communication line 90 such as the Internet in order to send later-described sorting information D to the sorting device 30. Moreover, the controller 24 is connected to the controller 33 of the sorting device 30 by a dedicated signal line 91 in order to send a later-described reference signal S to the sorting device 30.

The controller 24 detects the timings when the inspection articles P pass over the line sensor 23 based on the X-ray transmission signals sent from the line sensor 23. When the inspection articles P pass through the fan-shaped X-ray emission range Y, the controller 24 acquires, for each fixed moving distance of the inspection articles P (each imaging width u), the X-ray transmission signals corresponding to that moving distance (equivalent to one line) from the line sensor 23. In a case where the moving speed of the inspection articles P (the conveyance speed of the conveyance device 10) is fixed, the controller 24 acquires from the line sensor 23 the X-ray transmission signals at every fixed time interval. Additionally, the controller 24, particularly the control component 24d, creates the X-ray images of the inspection articles P based on the X-ray transmission signals acquired from the line sensor 23.

The control component 24d image-processes the X-ray images and judges, by plural judgment methods, the non-defective/defective of the inspection articles P (whether or not the inspection articles P are contaminated with foreign matter). Examples of the judgment methods include the trace detection method, the binarization detection method, and the mask binarization detection method. For example, the trace detection method is a method in which a threshold value is set beforehand along the approximate thickness of the inspection articles P and the inspection article P is judged being contaminated with foreign matter in a case where a region that appears darker than the threshold value exists in an X-ray image. For example, the binarization detection method is a method in which the inspection article P is judged being contaminated with foreign matter in a case where a region that appears darker than a threshold value set beforehand exists in an X-ray image of the inspection article P.

Moreover, the control component 24d generates, based on the results of the foreign matter inspection, unit sorting information d relating to the sorting of the inspection articles P for a segment with a predetermined width L along the conveyance direction of the conveyance device 10. The unit sorting information d is information representing the positions of inspection articles P contaminated with foreign matter on the conveyance surface of the conveyor belt 11 that has passed over the line sensor 23 in a period from the rise to the fall of a later-described reference signal S outputted by the reference signal sending component 24*b* or in a period from the fall to the rise of the reference signal S. As described later, the reference signal S is a signal that is switched on or off each time the conveyance distance of the conveyance device 10 becomes equal to the width L (a distance equivalent to N lines of single imaging width u of the line sensor 23).

Figure 5:
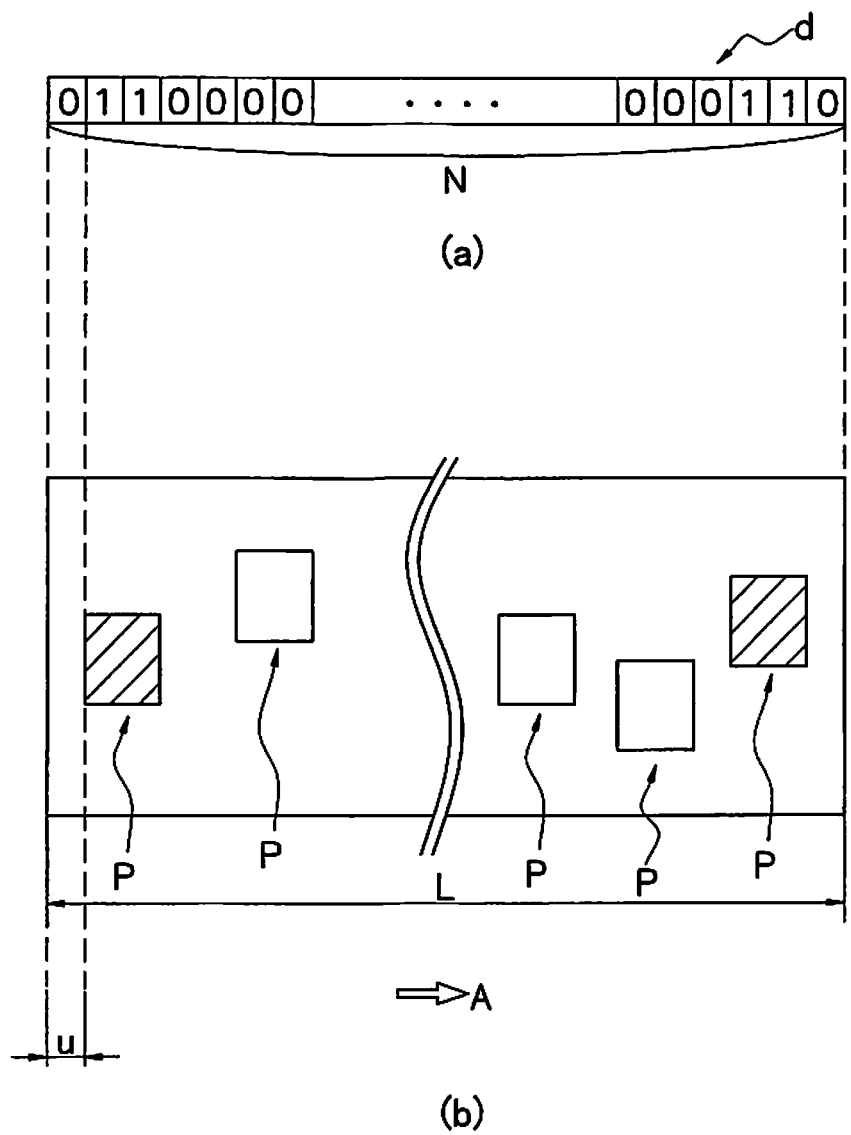
FIG. 5 is a drawing for describing unit sorting information generated by the X-ray inspection device of the inspection and sorting system of FIG. 1.

This will be specifically described using FIG. 5. For example, it is supposed that inspection articles P are placed like in FIG. 5(*b*) on the conveyor belt 11 that has passed over the line sensor 23 in a period from the fall to the rise of the reference signal S. Additionally, it is also supposed that the control component 24*d* has judged that the inspection articles P to which diagonal lines are added in FIG. 5(*b*) are contaminated with foreign matter.

In this case, the control component 24*d* divides the width L into N sections (divides the width L by every single imaging width u of the line sensor 23) and determines whether or not there exists, in each of the sections into which the width L is divided, the inspection article P judged as being contaminated with foreign matter. Then, the control component 24*d* uses the determination results to generate unit sorting information d where each of the sections into which the width L has been divided is expressed as one bit (see FIG. 5(*a*)). In the unit sorting information d, a bit expressed as "1" represents that an inspection article P contaminated with foreign matter exists in the position corresponding to that bit. On the other hand, a bit expressed as "0" represents that an inspection article P contaminated with foreign matter does not exist in the position corresponding to that bit.

The generated unit sorting information d is stored in the storage component 24*c* of the controller 24. Furthermore, when the unit sorting information d is generated, the sorting information sending component 24*a* sends, via the communication line 90, sorting information D to the controller 33 of the sorting device 30 described later. The sorting information D is information, relating to the sorting of the inspection articles P, in which the unit sorting information d that has just been generated and plural (in the present embodiment, four) sets of unit sorting information d of segments on the downstream side of the generated unit sorting information d as viewed from the conveyance direction of the conveyance device 10 are connected together. That is to say, the sorting information D is information representing the positions of inspection articles P contaminated with foreign matter in an interval spanning a distance of five times the width L.

In the present embodiment, the sorting information D is information for an interval spanning a distance of five times the width L because a distance of five times the width L is substantially equal to the distance, as seen in a plan view, from the line sensor 23 to a nozzle 32 of the air sorting mechanism 31 of the sorting device 30 described later. However, in actuality the distance from the line sensor 23 to the nozzle 32 is given by (width L×5+delay adjustment width α). The reason why the distance from the line sensor 23 to the nozzle 32 is not a distance of five times the width L but deviates therefrom by the delay adjustment width α will be described later.

It should be noted that the distance from the line sensor 23 to the nozzle 32 of the air sorting mechanism 31 is an exemplification and is not limited to this. For example, the distance from the line sensor 23 to the nozzle 32 of the air sorting mechanism 31 may also be (M (where M is an arbitrary integer) times the width L+delay adjustment width α). In this case, the sorting information D may be information of an interval spanning a distance of M times the width L.

(2-2-5-1) Reference Signal Sending Component

The reference signal sending component 24*b* outputs a fixed-interval reference signal S relating to the conveyance by the conveyance device 10. The transmission of the reference signal S by the reference signal sending component 24*b* is a process performed independently of the process of the foreign matter inspection.

The reference signal sending component 24*b* switches on/off of the reference signal S, based on the data that the controller 24 acquires from the encoder 13, each time the conveyance distance of the conveyance device 10 becomes equal to the predetermined width L (a distance equivalent N lines of single imaging widths u of the line sensor 23). That is to say, when the conveyance device 10 starts driving and conveys the conveyor belt 11 a distance equal to the width L, the reference signal sending component 24*b* sends the reference signal S from that point in time until the conveyance device 10 further conveys the conveyor belt 11 a distance equal to the width L. Thereafter, the reference signal sending component 24*b* stops sending the reference signal S and stands by until the conveyance device 10 further conveys the conveyor belt 11 a distance equal to the width L, and when the conveyance device 10 finishes conveying the conveyor belt 11 a distance equal to the width L, the reference signal sending component 24*b* again starts sending the reference signal S. The reference signal sending component 24*b* repeatedly performs these operations. That is to say, the reference signal S is a signal which, each time the conveyance device 10 conveys the conveyor belt 11 a distance of two times the width L, is transmitted while the conveyance device 10 conveys the conveyor belt 11 a distance equal to the width L. In other words, the reference signal S is a signal that is switched on or off each time the conveyance distance of the conveyance device 10 becomes equal to the width L.

The reference signal S is, as described above, a signal transmitted independently of the process of the foreign matter inspection. The reference signal sending component 24*b* therefore transmits the reference signal S without any lag (without the reference signal S being advanced or delayed) relative to the conveyance distance of the conveyor belt 11.

(2-3) Sorting Device

The sorting device 30 is a device that sorts the inspection articles P based on the results of the foreign matter inspection by the X-ray inspection device 20. Specifically, the sorting device 30 is a device that removes, from the conveyor belt 11 of the conveyance device 10, inspection articles P judged as being contaminated with foreign matter as a result of the foreign matter inspection by the X-ray inspection device 20.

The sorting device 30 mainly has the air sorting mechanism 31 and the controller 33 (see FIG. 4).

(2-3-1) Air Sorting Mechanism

The air sorting mechanism 31 is an example of a sorting mechanism that executes a sorting operation that sorts the inspection articles P conveyed by the conveyance device 10. The air sorting mechanism 31 sorts the inspection articles P conveyed by the conveyor belt 11 upon receiving a command from a sorting mechanism control component 33d of the controller 33.

The air sorting mechanism 31 mainly has the nozzle 32 (see FIG. 1) and an electromagnetic valve (not shown in the drawings) that opens and closes an air pathway that supplies high-pressure air to the nozzle 32. Since electromagnetic valves are convention electro-mechanical devices, further description is omitted for the sake of brevity.

The nozzle 32 is attached diagonally above the conveyance surface of the conveyor belt 11 of the conveyance device 10. The nozzle 32 is attached so as to discharge the high-pressure air in a direction intersecting the conveyance direction of the conveyance device 10, particularly a direction orthogonal to the conveyance direction, as viewed in a plan view. When the electromagnetic valve is opened by a command from the sorting mechanism control component 33d, the high-pressure air comes out from the nozzle 32 onto the inspection article P on the conveyor belt 11 and the inspection article P is removed to the outside of the conveyor belt 11 (e.g., to the inside of a box placed under the conveyor belt 11).

It should be noted that, from the time when the air sorting mechanism 31 receives the command to discharge the high-pressure air from the sorting mechanism control component 33d to until the time when the air sorting mechanism 31 actually blows out the air, the operation of the air sorting mechanism 31 is delayed a fixed amount of time Td due to individual response characteristics and tolerances of the air sorting mechanism 31 (e.g., the response characteristics and tolerances of the electromagnetic valve).

(2-3-2) Controller

The controller 33 is a computer that controls each part of the sorting device 30. The controller has a CPU that performs calculation and control, a ROM, a RAM, a hard disk and the like that serve as storage components storing information.

The controller 33 has a sorting information receiving component 33a and a reference signal receiving component 33b that receive information/signals from the controller 24 of the X-ray inspection device 20 (see FIG. 4). Furthermore, the controller 33 has a storage component 33c and a sorting mechanism control component 33d (see FIG. 4). The sorting mechanism control component 33d mainly has a CPU and executes a program stored in the storage component 33c to thereby cause the air sorting mechanism 31 to execute the sorting operation that sorts the inspection articles P. The storage component 33c stores the program executed by the sorting mechanism control component 33d and various types of information. The storage component 33c includes a sorting information storage region 33ca, which stores the sorting information D sent from the X-ray inspection device 20, and a sorting operation storage region 33cb, which is used when the sorting mechanism control component 33d causes the air sorting mechanism 31 to execute the sorting operation. The information stored in the sorting operation storage region 33cb is the aforementioned unit sorting information d.

The controller 33 is electrically connected to the air sorting mechanism 31. Furthermore, the controller 33 is also electrically connected to the encoder 13 of the conveyance device 10 (see FIG. 4). The controller 33 acquires data relating to the rotation speed of the conveyor motor 12 from the encoder 13 and grasps, based on the acquired data, the conveyance distance and conveyance speed of the inspection articles P.

Furthermore, the controller 33 is connected to the controller 24 of the X-ray inspection device 20 by the communication line 90 in order to receive the sorting information D (see FIG. 4). Moreover, the controller 33 is connected to the controller 24 of the X-ray inspection device 20 by the signal line 91 in order to receive the reference signal S from the controller 24 of the X-ray inspection device 20 (see FIG. 4).

(2-3-2-1) Sorting Information Receiving Component

The sorting information receiving component 33a is an example of a first receiving component. The sorting information receiving component 33a receives the sorting information D, which relates to the sorting of the inspection articles P based on the inspection results of the X-ray inspection device 20 and is sent by the sorting information sending component 24a of the controller 24 of the X-ray inspection device 20. The sorting information D sent by the sorting information sending component 24a is, as described above, information where five sets of the unit sorting information d are connected together. As described above, because the unit sorting information d is N bits of information, the sorting information D sent by the sorting information sending component 24a is (N×5) bits of information. When the sorting information receiving component 33a receives the sorting information D, the sorting information D is stored in the sorting information storage region 33ca.

It should be noted that the timing when the sorting information receiving component 33a receives the sorting information D is not fixed each time. This is, for example, because variations arise in the execution time of the foreign matter inspection necessary for the generation of the unit sorting information d by the control component 24d of the controller 24.

As described above, the sorting information D is information where the five sets of unit sorting information d that have been most recently generated are connected together. For example, it is supposed that at a certain point in time the sorting information receiving component 33a receives sorting information D including sets of unit sorting information d1, d2, d3, d4, and d5. It should be noted that, here, the sets of unit sorting information are denoted in such a way that the smaller the integer added thereto is older (the further downstream in the conveyance direction) set of unit sorting information. In this case, the sorting information D that the sorting information receiving component 33a will receive the next time is sorting information D including sets of unit sorting information d2, d3, d4, d5, and d6. That is to say, the sorting information D that the sorting information receiving component 33a receives at a certain point in time includes information redundant with the sorting information D that the sorting information receiving component 33a has received before.

With this configuration, even if a communication error were to occur so that at a certain timing the sorting information storage region 33ca receives incomplete sorting information D (in which some unit sorting information d is missing), the missing information can be compensated with the sorting information D that the sorting information storage region 33ca have received in the past or that the sorting information storage region 33ca will receive from the next time on.

(2-3-2-2) Reference Signal Receiving Component

The reference signal receiving component 33b receives the fixed-interval reference signal S relating to the conveyance by the conveyance device 10. The reference signal S is, as described above, a signal which, each time the conveyance device 10 conveys the conveyor belt 11 a distance of two times the width L, is transmitted while the conveyance device 10 conveys the conveyor belt 11 a distance equal to the width L. It should be noted that in a case where the conveyance speed of the conveyance device 10 is fixed, the reference signal S is a signal sent from the reference signal sending component 24b each fixed amount of time.

(2-3-2-3) Storage Component (2-3-2-3-1) Sorting Information Storage Region

The sorting information D received by the sorting information receiving component 33a is stored in the sorting information storage region 33ca. The sorting information D is, as described above, (N×5) bits of information where five sets of the unit sorting information d are connected together. When the sorting information receiving component 33a receives the sorting information D, the content stored in the sorting information storage region 33ca is rewritten to the received (most recent) sorting information D.

(2-3-2-3-2) Sorting Operation Storage Region

The set of unit sorting information d furthest downstream in the conveyance direction of the conveyance device 10, or in other words the oldest N bits of information in terms of the time series, in the sorting information D stored in the sorting information storage region 33ca is written to the sorting operation storage region 33cb by a sorting operation storage rewriting component 33da of the sorting mechanism control component 33d described later and stored in the sorting operation storage region 33cb. The content of the sorting operation storage region 33cb is rewritten at a timing adjusted by the reference signal S received by the reference signal receiving component 33b.

(2-3-2-4) Sorting Mechanism Control Component

The sorting mechanism control component 33d controls the air sorting mechanism 31 to execute the sorting operation based on the sorting information D received by the sorting information receiving component 33a at a timing adjusted by the reference signal S received by the reference signal receiving component 33b.

The sorting mechanism control component 33d mainly has, as sub-function components, a sorting operation storage rewriting component 33da and a command generating component 33db (see FIG. 4).

(2-3-2-4-1) Sorting Operation Storage Rewriting Component

The sorting operation storage rewriting component 33da rewrites the content stored in the sorting operation storage region 33cb based on the sorting information D stored in the sorting information storage region 33ca at a timing adjusted by the reference signal S received by the reference signal receiving component 33b. As described later, when the content of the sorting operation storage region 33cb is rewritten, the command generating component 33db starts, at that timing, the control of the air sorting mechanism 31 based on the rewritten content. Therefore, the timing of the rewriting of the content of the sorting operation storage region 33cb determines the timing of the sorting operation of the air sorting mechanism 31.

The timing when the sorting operation storage rewriting component 33da rewrites the information in the sorting information storage region 33ca will be described in detail.

First, an operation delay of the air sorting mechanism 31 will be described. It is supposed that the air sorting mechanism 31 operates without delay when it receives a command to operate. In this case, the sorting mechanism control component 33d can send the command to discharge air to the air sorting mechanism 31 at the moment when the inspection article P to be sorted (contaminated with foreign matter) is conveyed in front of the nozzle 32.

However, in actuality, as described above, the air discharge operation is delayed owing to the activation time of the electromagnetic valve that switches between supplying and stopping the supply of the high-pressure air or the like. For that reason, the sorting mechanism control component 33d needs to send the command to discharge air to the air sorting mechanism 31 before the inspection article P to be sorted is conveyed in front of the nozzle 32. Therefore, the sorting device 30 is given, for controlling the air sorting mechanism 31, sorting information D prepared such that in a case where it is supposed that the air sorting mechanism 31 could operate without delay when it receives a command to operate, air would be discharged from the nozzle 32 when the inspection article P to be sorted passes a point located before the actual position of the nozzle 32 by the delay adjustment width α when controlling the air sorting mechanism 31 based on the sorting information D.

It should be noted that the delay adjustment width α is determined in such a way that, in a case where the conveyance speed of the conveyance device 10 is set to a maximum conveyance speed Vmax, by sending the air discharge command to the air sorting mechanism 31 when the inspection article P to be sorted is being conveyed at the point located before the position of the nozzle 32 by the delay adjustment width α in the conveyance direction, air will be discharged to the inspection article P to be sorted when that inspection article P passes in front of the nozzle 32.

The delay time Td, determined by the characteristics of the air sorting mechanism 31, from when the command to execute the sorting operation is received to when the sorting operation is actually executed is constant regardless of the conveyance speed of the conveyance device 10. The sorting operation storage rewriting component 33da determines, based on the fixed delay time Td determined by the characteristics of the air sorting mechanism 31, the timing when it rewrites the information in the sorting information storage region 33ca. It should be noted that the delay time Td is given by (delay adjustment width α/maximum conveyance speed Vmax).

For example, in a case where the conveyance speed of the conveyance device 10 acquired based on the data sent from the encoder 13 is the maximum conveyance speed Vmax, the sorting operation storage rewriting component 33da rewrites the information in the sorting information storage region 33ca at the timing when the reference signal S received by the reference signal receiving component 33b rises (when the reference signal switches from off to on) or when the reference signal S falls (when the reference signal switches from on to off).

For example, in a case where the conveyance speed of the conveyance device 10 acquired based on the data sent from the encoder 13 is a conveyance speed V (V<Vmax), the sorting operation storage rewriting component 33da rewrites the information in the sorting information storage region 33ca after the elapse of {(delay adjustment width α/conveyance speed V)−delay time Td} from the point in time when the reference signal S received by the reference signal receiving component 33b rises or falls.

(2-3-2-4-2) Command Generating Component

The command generating component 33db generates a command to the air sorting mechanism 31 using the content stored in the sorting operation storage region 33cb and sends the command to the air sorting mechanism 31. Specifically, at the timing when the content of the sorting operation storage region 33cb is rewritten, the command generating component 33db generates a command for the air sorting mechanism 31 and sends the command to the air sorting mechanism 31, so that the air sorting mechanism 31 executes the operation according to the time series information stored in the sorting operation storage region 33*cb* in order starting from the beginning of the time series. This will be described specifically below.

As described above, the information written in the sorting operation storage region 33*cb* is the unit sorting information d generated by the X-ray inspection device 20, and is N bits of binary information. When the value of the bit is "1", the command generating component 33*db* generates a command to discharge air and sends it to the air sorting mechanism 31. When the value of the bit is "0", the command generating component 33*db* generates a command prohibiting the discharge of air and sends it to the air sorting mechanism 31. It should be noted that the time in which the air sorting mechanism 31 discharges air or prohibits the discharge of air based on each bit of information is the time in which the conveyance device 10 conveys the inspection article P by a distance given by (width L/N) or in other words by a single imaging width u of the line sensor 23. That is to say, the time in which the air sorting mechanism 31 discharges air or prohibits the discharge of air based on each bit of information is a time obtained by dividing the distance given by (width L/N) by the conveyance speed V of the conveyance device 10. It should be noted that the width L here is, as described above, a predetermined distance along the conveyance direction of the conveyance device 10 for which the control component 24*d* of the X-ray inspection device 20 generates a unit sorting information d. N is the number of bits of the unit sorting information d.

This will be described by way of a specific example. For example, it is supposed that the information shown in FIG. 5(*a*) has been written in the sorting operation storage region 33*cb*. It should be noted that, in FIG. 5(*a*), the further to the right the information is, the further downstream the information is in the conveyance direction. In this case, the value of the first bit from the rightmost is "0", so the command generating component 33*db* generates a command prohibiting the discharge of air from the air sorting mechanism 31 for a time (width L/(N×conveyance speed V)) obtained by dividing the distance given by (width L/N) by the conveyance speed V of the conveyance device 10. Next, the value of the second bit from the rightmost is "1", so the command generating component 33*db* generates a command causing the air sorting mechanism 31 to execute air discharge for a time (width L/(N×conveyance speed V)). The command generating component 33*db* executes this process in succession until it finishes generating a command based on the value of the Nth bit from the rightmost or the information in the sorting operation storage region 33*cb* is updated next.

(3) Process Executed by Sorting Device

Figure 6:
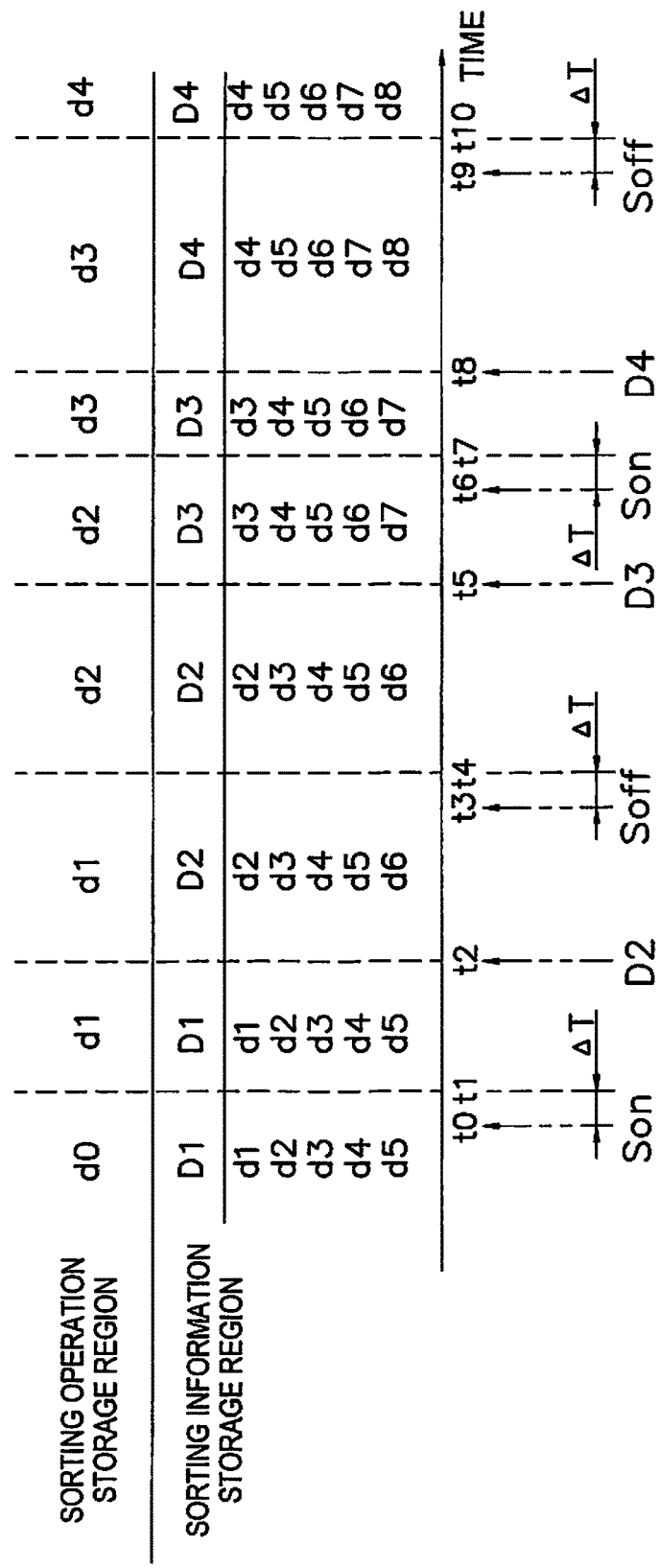
FIG. 6 is a drawing for describing the timing of a process of rewriting a sorting operation storage region and a sorting information storage region in a sorting device of the inspection and sorting system of FIG. 1.

The process executed by the sorting device 30, and particularly the process of rewriting the sorting information storage region 33*ca* and the sorting operation storage region 33*cb*, will be described using FIG. 6.

First, as a premise, it is supposed that at a given time (point in time t0 in FIG. 6) the sorting information D1 including the sets of unit sorting information d1 to d5 is stored in the sorting information storage region 33*ca*. It should be noted that the smaller the numbers added to the sets of unit sorting information d1 to d5 are, the further downstream the information is in the conveyance direction of the conveyance device 10 (in other words, the older the information is). Furthermore, it is supposed that at the point in time t0 in FIG. 6 the sorting mechanism control component 33*d* detects the rise of the reference signal S (expressed as Son in FIG. 6) received by the reference signal receiving component 33*b*. It should be noted that, here, it is supposed that the conveyance speed of the conveyance device 10 is fixed at the conveyance speed V.

In this case, the sorting operation storage rewriting component 33*da* rewrites the content of the sorting operation storage region 33*cb* from the unit sorting information d0 that has been stored until then to the oldest set of unit sorting information d1 in the sorting information D1 at time t1 after the elapse of {(delay adjustment width α/conveyance speed V)−delay time Td} (hereinafter, the value of {(delay adjustment width α/conveyance speed V)−delay time Td} will be expressed as Δt) from t0 when the rise of the reference signal S is detected. When the content of the sorting operation storage region 33*cb* is rewritten, the command generating component 33*db* starts controlling the air sorting mechanism 31 in accordance with the newly rewritten unit sorting information d1 at the timing of the rewriting of the sorting operation storage region 33*cb*.

Thereafter, at a given time t2, the sorting information receiving component 33*a* receives sorting information D2 including sets of unit sorting information d2 to d6. At this time, the content of the sorting information storage region 33*ca* is rewritten from the sorting information D1 to the newly received sorting information D2. At this time, the content of the sorting operation storage region 33*cb* is not changed. In this way, the timing of the reception of the sorting information D does not affect the timing of the rewriting of the sorting operation storage region 33*cb*. Therefore, even if the timing of the reception of the sorting information D varies, this does not affect the timing when the sorting device 30 executes the sorting operation of the inspection articles P.

Next, when at a given time t3 the fall of the reference signal S (expressed as Soff in FIG. 6) received by the reference signal receiving component 33*b* is detected, at time t4 after the elapse of Δt from the time t3, the content of the sorting operation storage region 33*cb* is rewritten from the unit sorting information d1 that has been stored until then to the oldest set of unit sorting information d2 in the sorting information D2 stored in the sorting information storage region 33*ca*. When the content of the sorting operation storage region 33*cb* is switched, the command generating component 33*db* starts controlling the air sorting mechanism 31 in accordance with the newly rewritten unit sorting information d2 at the timing of the rewriting of the sorting operation storage region 33*cb*.

As what follows thereafter is similar, description thereof will be omitted.

It should be noted that, here, because it is supposed that the conveyance speed of the conveyance device 10 is fixed at the conveyance speed V, the rise or fall of the reference signal S that is switched on or off each time the conveyance distance of the conveyance device 10 becomes equal to the width L occurs at a fixed time interval. Therefore, in a case where the conveyance speed V is not changed, a reference signal S sent at fixed conveyance time interval may be used instead. Furthermore, because the conveyance speed of the conveyance device 10 is fixed at the conveyance speed V, Δt also becomes a fixed value.

However, the conveyance speed of the conveyance device 10 does not need to be fixed, and the conveyance speed of the conveyance device 10 may vary. In a case where the conveyance speed varies, the rise or fall of the reference signal S does not occur at a fixed time interval, and the rise or fall of the reference signal S is detected each time the conveyance distance of the conveyance device 10 becomes equal to the width L. Furthermore, in a case where the conveyance speed of the conveyance device 10 is not fixed, Δt becomes appropriately changed.

(4) Characteristics (4-1)

The inspection and sorting system 100 pertaining to the first embodiment is provided with the conveyance device 10 serving as an example of a conveying means, the X-ray inspection device 20 serving as an example of an inspection device, and the sorting device 30. The conveyance device 10 conveys the inspection articles P (articles). The X-ray inspection device 20 inspects the inspection articles P conveyed by the conveyance device 10. The sorting device 30 has the air sorting mechanism 31 that executes the sorting operation in which the inspection articles P conveyed by the conveyance device 10 are sorted. The air sorting mechanism 31 is an example of a sorting mechanism. The sorting device 30 has the sorting information receiving component 33a serving as an example of a first receiving component, the reference signal receiving component 33b serving as example of a second receiving component, and the sorting mechanism control component 33d. The sorting information receiving component 33a receives the sorting information D relating to the sorting of the inspection articles P based on the inspection results of the X-ray inspection device 20. The reference signal receiving component 33b receives the fixed-interval reference signal S relating to the conveyance by the conveyance device 10. The sorting mechanism control component 33d controls the air sorting mechanism 31 to execute the sorting operation based on the sorting information D at a timing adjusted by the reference signal S.

In this inspection and sorting system 100, the air sorting mechanism 31 executes the sorting operation based on the fixed-interval reference signal S relating to the conveyance by the conveyance device 10 for adjusting the timing of the execution of the sorting operation as well as the sorting information relating to the sorting. For that reason, the sorting operation can be executed at an appropriate timing regardless of variations in the reception timing of the sorting information D. As a result, the inspection articles P conveyed from the X-ray inspection device 20 can be sorted, based on the inspection results, at a high processing speed and with good precision.

It should be noted that it is also conceivable to provide a separate photoelectric sensor or the like as another measure to adjust the timing of the execution of the sorting operation. However, for example, in a case where there are variations in the height of the inspection articles P, chattering of the photoelectric sensor is often caused if the inspection articles P are detected with the photoelectric sensor and the inspection articles P to be sorted may be misidentified. Furthermore, providing a separate photoelectric sensor leads to an increase in the manufacturing cost of the inspection and sorting system. In that respect, in the inspection and sorting system 100 of the above embodiment, it is easy to suppress the occurrence of misidentification of the inspection articles P to be sorted because the sorting operation of the air sorting mechanism 31 is not affected by the height of the inspection articles P.

(4-2)

In the inspection and sorting system 100 pertaining to the above embodiment, the reference signal S is a signal transmitted to the reference signal receiving component 33b while the conveyance device 10 conveys the width L, each time the conveyance device 10 conveys a distance (a first distance) of two times the width L.

Here, the reference signal receiving component 33b receives the reference signal S each time the conveyance device 10 conveys a fixed distance. The inspection articles P conveyed from the X-ray inspection device 20 can be therefore sorted at a high processing speed and with good precision based on a timing adjusted by the reference signal S and the inspection results of the X-ray inspection device 20.

(4-3)

In the inspection and sorting system 100 pertaining to the above embodiment, the X-ray inspection device 20 has the line sensor 23. The line sensor 23 images, in every single imaging, a predetermined width (the imaging width u) along the conveyance direction of the conveyance device. The distance (the first distance) of two times the width L is an integral multiple of the predetermined width. Specifically, the distance of two times the width L is N×2 times the imaging width u.

Here, the reference signal S is sent each time the conveyance distance of the conveyance device 10 becomes equal to the integral multiple of the predetermined width (the imaging width u) for which the line sensor 23 of the X-ray inspection device 20 images. It is therefore easy to execute the sorting operation at an appropriate timing matching the inspection results of the X-ray inspection.

(4-4)

In the inspection and sorting system 100 pertaining to the above embodiment, the X-ray inspection device 20 inspects the non-defective/defective of the inspection articles P by performing a foreign matter inspection of the inspection articles P.

Here, the inspection articles P can be sorted by the sorting device 30 based on the non-defective/defective of the inspection articles P.

(4-5)

In the inspection and sorting system 100 pertaining to the above embodiment, the timing when the air sorting mechanism 31 executes the sorting operation based on the sorting information D is determined based on the fixed delay time Td determined by the characteristics of the air sorting mechanism 31. Specifically, the timing is adjusted from the point in time of the rise or fall of the reference signal S by a time calculated as {(delay adjustment width α/conveyance speed V of conveyance device 10)−delay time Td}.

Here, the timing of the sorting operation of the air sorting mechanism 31 is determined based on the fixed delay time Td determined by the characteristics of the air sorting mechanism 31. Therefore, even in a case where the conveyance speed V of the conveyance device 10 is changed, the sorting operation can be executed at an appropriate timing.

Second Embodiment

An inspection and sorting system 200 pertaining to a second embodiment of the present invention will be described.

(1) Overall Configuration

The inspection and sorting system 200 pertaining to the second embodiment is a system that inspects the rank of inspection articles P (articles), such as food articles, being conveyed and sorts the inspection articles P based on the inspection results. Specifically, the inspection and sorting system 200 sorts the inspection articles P by rank according to their weight based on the results of a weight estimation of the inspection articles P.

Figure 7:
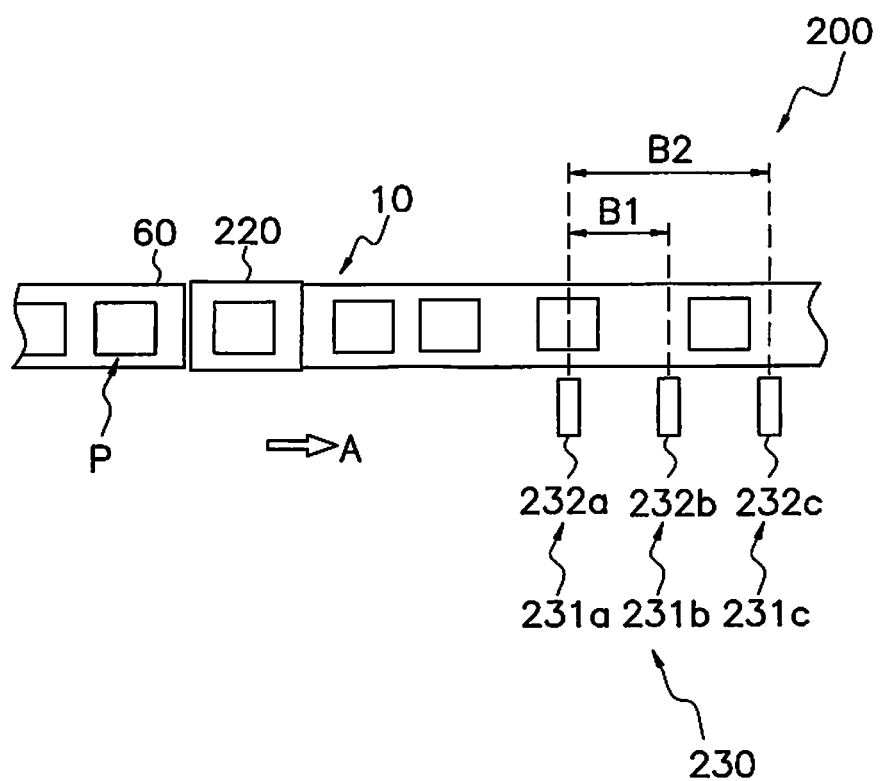
FIG. 7 is a schematic diagram of an inspection and sorting system pertaining to a second embodiment of the present invention.

The inspection and sorting system 200 is mainly provided with a conveyance device 10, an X-ray inspection device 220, and a sorting device 230 (see FIG. 7).

The conveyance device 10 is the same as the one in the first embodiment, so description thereof will be omitted.

The X-ray inspection device 220 performs a weight estimation of the inspection articles P conveyed by the conveyance device 10 and classifies the inspection articles P into plural ranks (here, three ranks) in accordance with their weight. The sorting device 230 executes a sorting operation that sorts the inspection articles P conveyed by the conveyance device 10 based on the inspection results of the X-ray inspection device 220.

(2) Detailed Configuration

The X-ray inspection device 220 and the sorting device 230 of the inspection and sorting system 200 will be described below in detail.

(2-1) X-Ray Inspection Device

The X-ray inspection device 220 is an example of an inspection device that inspects the inspection articles P conveyed by the conveyance device 10. The X-ray inspection device 220 irradiates X-ray to the inspection articles P continuously conveyed by the conveyance device 10, estimates the weights of the inspection articles P based on the amount of X-ray that has been transmitted through the inspection articles P, and classifies the inspection articles P into three ranks according to their weights.

Figure 8:
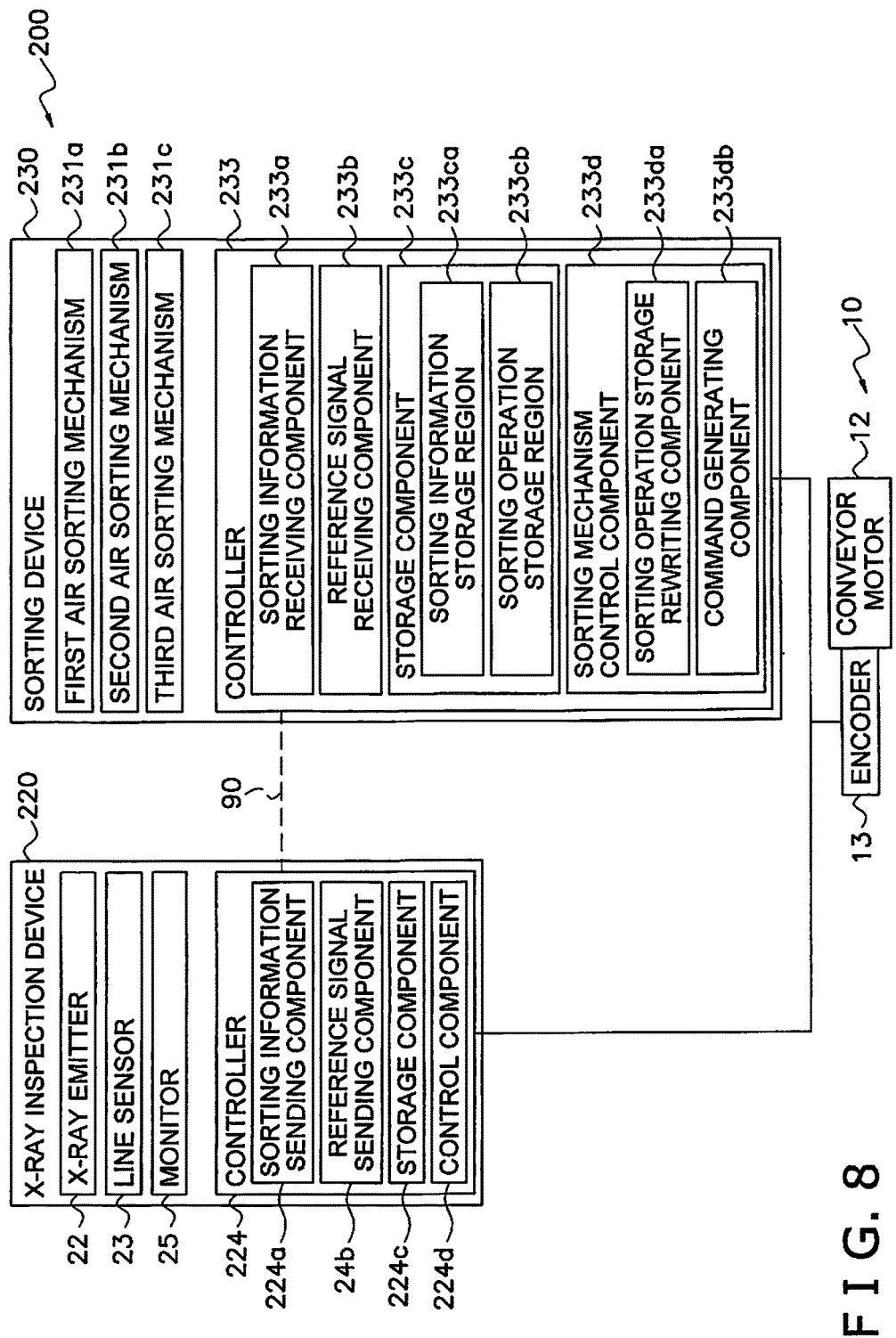
FIG. 8 is a block diagram of the inspection and sorting system of FIG. 7.

The X-ray inspection device 220 mainly has a shield box 21, an X-ray emitter 22, a line sensor 23, a monitor 25 having a touch panel function, and a controller 224 (see FIG. 8). The shield box 21, the X-ray emitter 22, and the monitor 25 having the touch panel function are the same as the ones in the X-ray inspection device 20 of the first embodiment, so description thereof will be omitted. The line sensor 23 is also the same except that the X-ray transmission signal is used for the weight estimation of the inspection articles P rather than for a foreign matter inspection of the inspection articles P, so description thereof will be omitted.

(2-1-1) Controller

The controller 224 is a computer that controls each part of the X-ray inspection device 220. The controller 224, like the controller 24 of the first embodiment, has a CPU that performs calculation and control, a ROM, a RAM, a hard disk and the like that serve as storage components storing information.

The controller 224 has a sorting information sending component 224a and a reference signal sending component 24b that send information/signals to a controller 233 of the sorting device 230 described later (see FIG. 8). It should be noted that the reference signal sending component 24b is the same as the one in the first embodiment, so description thereof will be omitted below. The controller 224 has a storage component 224c and a control component 224d (see FIG. 8). The control component 224d mainly has a CPU and executes a program stored in the storage component 224c to thereby generate X-ray images, estimate the weights of the inspection articles P based on the generated X-ray images, and determine rank based on the estimated weights. Furthermore, the control component 224d controls the operation of each part of the X-ray inspection device 220, such as the X-ray emitter 22 and the line sensor 23. Various inspection parameters used in the rank inspection are stored in the storage component 224c. For example, a weight conversion table for converting the gray scale values of the X-ray images into weight values and plural threshold values (here, two threshold values) for determining rank in accordance with the weights of the inspection articles P are stored in the storage component 224c. Furthermore, later-described unit sorting information e generated by the control component 224d as a result of the rank inspection of the inspection articles P is stored in the storage component 224c.

The controller 224 is electrically connected to the X-ray emitter 22, the line sensor 23, and the monitor 25. Furthermore, the controller 224 is also electrically connected to the conveyor motor 12 and the encoder 13 of the conveyance device 10 (see FIG. 8). The controller 224 acquires data relating to the rotation speed of the conveyor motor 12 from the encoder 13 and grasps, based on the acquired data, the conveyance distance and conveyance speed of the inspection articles P.

Furthermore, the controller 224 is connected to the controller 233 of the sorting device 230 by a communication line 90 such as the Internet in order to send later-described sorting information E and a reference signal S to the sorting device 230 (see FIG. 8). In contrast to the controller 24 of the first embodiment, the dedicated signal line 91 is not used for connecting the controller 224 to the controller 233 of the sorting device 230.

The controller 224 detects the timings when the inspection articles P pass over the line sensor 23 based on the X-ray transmission signals sent from the line sensor 23. When the inspection articles P pass through the fan-shaped X-ray emission range Y, the controller 224 acquires, for each fixed moving distance of the inspection articles P (each imaging width u), the X-ray transmission signals corresponding to that moving distance (equivalent to one line) from the line sensor 23. In a case where the moving speed of the inspection articles P (the conveyance speed of the conveyance device 10) is fixed, the controller 224 acquires from the line sensor 23 the X-ray transmission signals at every fixed time interval. Additionally, the controller 224, particularly the control component 224d, creates the X-ray images of the inspection articles P based on the X-ray transmission signals acquired from the line sensor 23.

The control component 224d performs, based on the X-ray images of the inspection articles P, a weight estimation of those inspection articles P. Specifically, the control component 224d creates, based on the gray scale value of each pixel configuring the X-ray image of the inspection article P, a histogram representing a number of pixels for every gray scale value. Thereafter, the controller 224 uses the created histogram and the weight conversion table stored in the storage component 224c to add the weight values corresponding to all the pixels together and estimate the weights of the inspection articles P. Moreover, the controller 224 compares the estimated weights of the inspection articles P with the two threshold values stored in the storage component 224c to thereby classify the inspection articles into three ranks.

Moreover, the control component 224d generates, based on the results of the rank inspection, unit sorting information e relating to the sorting of the inspection articles P for a segment with a predetermined width L along the conveyance direction of the conveyance device 10. The unit sorting information e is information representing the positions and ranks of the inspection articles P on the conveyance surface of the conveyor belt 11 that has passed over the line sensor 23 in a period from the rise to the fall of the reference signal S outputted by the reference signal sending component 24b or in a period from the fall to the rise of the reference signal S.

Figure 9:
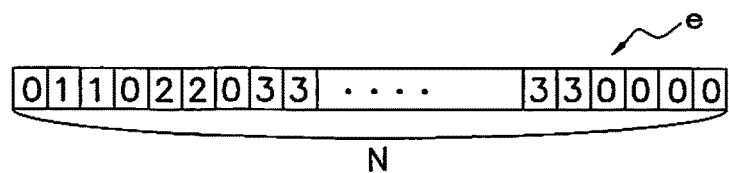
FIG. 9 is an example of unit sorting information generated by an X-ray inspection device of the inspection and sorting system of FIG. 7.

In the first embodiment the unit sorting information d was N bits of binary (expressed as "0" or "1") information, but the unit sorting information e differs in that it is N number of multi-value (expressed as "0", "1", "2", and "3") information (see FIG. 9). This is because in the first embodiment it sufficed for the unit sorting information d to express only whether or not there exist inspection articles P contaminated with foreign matter, but in the second embodiment, the unit sorting information e expresses which of the three ranks the inspection articles P belong to.

The control component 224d divides the width L into N number of sections (divides the width L by every single imaging width u of the line sensor 23) and determines whether there exists the inspection article P in each of the sections into which the width L has been divided, and, when there exists the inspection article P, the rank to which that inspection article P belongs. Additionally, the control component 224d generates unit sorting information e in which each divided section is expressed by one numerical value using the determination results. In the unit sorting information e, a numerical value of "0" means that an inspection article P does not exist in the position corresponding to that numerical value. Furthermore, in the unit sorting information e, a numerical value of "1", "2", or "3" means that an inspection article P belonging to a rank indicated by that numerical value exists in the position corresponding to that numerical value.

The generated unit sorting information e is stored in the storage component 224c of the controller 224. Furthermore, when the unit sorting information e is generated, the sorting information sending component 224a sends, via the communication line 90, sorting information E to the controller 233 of the sorting device 230 described later. The sorting information E is information, relating to the sorting of the inspection articles P, in which the unit sorting information e that has just been generated and plural (in the present embodiment, four) sets of unit sorting information e of segments on the downstream side of the generated unit sorting information e as viewed from the conveyance direction of the conveyance device 10 are connected together. That is to say, the sorting information E is information representing the positions and ranks of the inspection articles P in an interval spanning a distance of five times the width L.

(2-2) Sorting Device

The sorting device 230 performs sorting of the inspection articles P based on the results of the rank inspection by the X-ray inspection device 220. Specifically, the sorting device 230 sorts, based on the results of the rank inspection by the X-ray inspection device 220, the inspection articles P to three conveyors not shown in the drawings according to their rank.

The sorting device 230 mainly has first to third air sorting mechanisms 231a, 231b, and 231c and the controller 233 (see FIG. 8).

(2-2-1) Air Sorting Mechanisms

Each of the first to third air sorting mechanisms 231a, 231b, and 231c is the same as the air sorting mechanism 31 of the first embodiment. The first air sorting mechanism 231a has a first nozzle 232a and an electromagnetic valve (not shown in the drawings) that opens and closes an air pathway that supplies high-pressure air to the first nozzle 232a. The second air sorting mechanism 231b has a second nozzle 232b and an electromagnetic valve (not shown in the drawings) that opens and closes an air pathway that supplies high-pressure air to the second nozzle 232b. The third air sorting mechanism 231c has a third nozzle 232c and an electromagnetic valve (not shown in the drawings) that opens and closes an air pathway that supplies high-pressure air to the third nozzle 232c. The first to third air sorting mechanisms 231a, 231b, and 231c are mechanisms controlled independently of each other by the controller 233.

The first to third nozzles 232a, 232b, and 232c are attached diagonally above the conveyance surface of the conveyor belt 11 of the conveyance device 10. The first to third nozzles 232a, 232b, and 232c are attached so as to discharge the high-pressure air in a direction intersecting the conveyance direction (see the arrow A in FIG. 7) of the conveyance device 10, particularly a direction orthogonal to the conveyance direction, as viewed in a plan view. The first to third nozzles 232a, 232b, and 232c are installed in this order from the upstream side to the downstream side in the conveyance direction (see the arrow A in FIG. 7) of the conveyance device 10 (see FIG. 7). The first nozzle 232a and the second nozzle 232b are installed a distance B1 apart from each other, and the first nozzle 232a and the third nozzle 232c are installed a distance B2 apart from each other. When the electromagnetic valve of the first air sorting mechanism 231a, the second air sorting mechanism 231b, or the third air sorting mechanism 231c is opened by a command from a sorting mechanism control component 233d, the high-pressure air comes out from the first nozzle 232a, the second nozzle 232b, or the third nozzle 232c, respectively. Additionally, when the air is blown onto the inspection article P on the conveyor belt 11, the inspection article P is sorted to the non-illustrated corresponding conveyor disposed below the conveyor belt 11.

(2-2-2) Controller

The controller 233 is a computer that controls each part of the sorting device 230. The controller 233 has a CPU that performs calculation and control, a ROM, a RAM, and a hard disk, and the like that serve as storage components that store information.

The controller 233 has a sorting information receiving component 233a and a reference signal receiving component 233b that receive information/signals from the controller 224 of the X-ray inspection device 220 (see FIG. 8). Furthermore, the controller 233 has a storage component 233c and a sorting mechanism control component 233d (see FIG. 8). The sorting mechanism control component 233d mainly has a CPU and executes a program stored in the storage component 233c to thereby cause the first to third air sorting mechanisms 231a, 231b, and 231c to execute the sorting operation that sorts the inspection articles P. The storage component 233c stores the program executed by the sorting mechanism control component 233d and various types of information. The storage component 233c includes a sorting information storage region 233ca, which stores the sorting information E sent from the X-ray inspection device 220, and a sorting operation storage region 233cb, which is used when the sorting mechanism control component 233d causes the first to third air sorting mechanisms 231a, 231b, and 231c to execute the sorting operation. The information stored in the sorting information storage region 233cb is the aforementioned unit sorting information e.

The controller 233 is electrically connected to the first to third air sorting mechanisms 231a, 231b, and 231c. Furthermore, the controller 233 is also electrically connected to the encoder 13 of the conveyance device 10 (see FIG. 8). The controller 233 acquires data relating to the rotation speed of the conveyor motor 12 from the encoder 13 and grasps, based on the acquired data, the conveyance distance and conveyance speed of the inspection articles P.

Furthermore, the controller 233 is connected to the controller 224 of the X-ray inspection device 220 by the communication line 90 in order to receive the sorting information E and the reference signal S (see FIG. 8).

(2-2-2-1) Sorting Information Receiving Component

The sorting information receiving component 233a receives the sorting information E, which relates to the sorting of the inspection articles P based on the inspection results of the X-ray inspection device 220 and is sent by the sorting information sending component 224a of the controller 224 of the X-ray inspection device 220. The sorting information receiving component 233a is the same as the one in the first embodiment except that the content of the information it receives is different (the information the sorting information receiving component 233a receives is not the sorting information D but rather the sorting information E), so detailed description thereof will be omitted.

(2-2-2-2) Reference Signal Receiving Component

The reference signal receiving component 233b is the same as the one in the first embodiment, so description thereof will be omitted.

(2-2-2-3) Storage Component

(2-2-2-3-1) Sorting Information Storage Region

The sorting information E received by the sorting information receiving component 233a is stored in the sorting information storage region 233ca. The sorting information E is, as described above, information including (N×5) number of numerical values where five sets of the unit sorting information e are connected together. When the sorting information receiving component 233a receives the sorting information E, the content stored in the sorting information storage region 233ca is rewritten to the received (most recent) sorting information E.

(2-2-2-3-2) Sorting Operation Storage Region

The set of unit sorting information e furthest downstream in the conveyance direction of the conveyance device 10, or in other words the oldest N number of numerical value information in terms of the time series, in the sorting information E stored in the sorting information storage region 233ca is written to the sorting operation storage region 233cb by a sorting operation storage rewriting component 233da of the sorting mechanism control component 233d described later and stored in the sorting operation storage region 233cb. The content of the sorting operation storage region 233cb is rewritten at a timing adjusted by the reference signal S received by the reference signal receiving component 233b.

(2-2-2-4) Sorting Mechanism Control Component

The sorting mechanism control component 233d controls the first to third air sorting mechanisms 231a, 231b, and 231c to execute the sorting operation based on the sorting information E received by the sorting information receiving component 233a at the timing adjusted by the reference signal S received by the reference signal receiving component 233b.

The sorting mechanism control component 233d mainly has, as sub-function components, the sorting operation storage rewriting component 233da and a command generating component 233db (see FIG. 8).

(2-2-2-4-1) Sorting Operation Storage Rewriting Component

The sorting operation storage rewriting component 233da rewrites the content stored in the sorting operation storage region 233cb based on the sorting information E stored in the sorting information storage region 233ca at the timing adjusted by the reference signal S received by the reference signal receiving component 233b. As described later, when the content of the sorting operation storage region 233cb is rewritten, the command generating component 233db starts, at that timing, the control of the first to third air sorting mechanisms 231a, 231b, and 231c based on the rewritten content. Therefore, the timing of the rewriting of the content of the sorting operation storage region 233cb determines the timing of the sorting operation of the first to third air sorting mechanisms 231a, 231b, and 231c.

The timing when the sorting operation storage rewriting component 233da rewrites the information in the sorting information storage region 233ca will be described in detail.

Like the air sorting mechanism 31 of the aforementioned embodiment, in the first to third air sorting mechanisms 231a, 231b, and 231c, a delay also occurs between the time when the first to third air sorting mechanisms 231a, 231b, and 231c receive a command to operate and the time when the first to third air sorting mechanisms 231a, 231b, and 231c actually execute the operation. Therefore, the sorting device 230 is given, for controlling the first to third air sorting mechanisms 231a, 231b, and 231c, the sorting information E prepared such that in a case where it is supposed that the first air sorting mechanism 231a positioned furthest upstream in the conveyance direction could operate without delay when it receives a command to operate, air would be discharged from the first nozzle 232a when the inspection article P to be sorted by the first air sorting mechanism 231a passes a point located before the actual position of the first nozzle 232a by the delay adjustment width α when controlling the first air sorting mechanism 231a based on the sorting information E.

It should be noted that the delay adjustment width α is determined in such a way that, in a case where the conveyance speed of the conveyance device 10 is set to a maximum conveyance speed Vmax, by sending the air discharge command to the first air sorting mechanism 231a when the inspection article P to be sorted by the first air sorting mechanism 231a is being conveyed at the point located before the position of the first nozzle 232a by the delay adjustment width α in the conveyance direction, air will be discharged to the inspection article P to be sorted when that inspection article P to be sorted passes in front of the first nozzle 232a.

The delay time Td, determined by the characteristics of the first to third air sorting mechanisms 231a, 231b, and 231c, from when the command to execute the sorting operation is received to when the sorting operation is actually executed is fixed regardless of the conveyance speed of the conveyance device 10. The sorting operation storage rewriting component 33da determines, based on the fixed delay time Td determined by the characteristics of the first to third air sorting mechanisms 231a, 231b, and 231c, the timing when it rewrites the information in the sorting information storage region 233ca. It should be noted that the delay time Td is given by (delay adjustment width α/maximum conveyance speed Vmax).

For example, in a case where the conveyance speed of the conveyance device 10 acquired based on the data sent from the encoder 13 is the maximum conveyance speed Vmax, the sorting operation storage rewriting component 233da rewrites the information in the sorting information storage region 233ca at the timing when the reference signal S received by the reference signal receiving component 233b rises (when the reference signal switches from off to on) or when the reference signal S falls (when the reference signal switches from on to off).

For example, in a case where the conveyance speed of the conveyance device 10 acquired based on the data sent from the encoder 13 is the conveyance speed V (V<Vmax), the sorting operation storage rewriting component 233da rewrites the information in the sorting information storage region 233ca after the elapse of {(delay adjustment width α/conveyance speed V)−delay time Td} from the point in time when the reference signal S received by the reference signal receiving component 233b rises or falls.

(2-2-2-4-2) Command Generating Component

The command generating component 233db generates a command to the first to third air sorting mechanisms 231a, 231b, and 231c with the content stored in the sorting operation storage region 233cb and sends the command to the first to third air sorting mechanisms 231a, 231b, and 231c. Specifically, at the timing when the content of the sorting operation storage region 233cb is rewritten, the command generating component 233db generates a command for the first to third air sorting mechanisms 231a, 231b, and 231c and sends the command to the first to third air sorting mechanisms 231a, 231b, and 231c, so that the first to third air sorting mechanisms 231a, 231b, and 231c execute the operation according to the time series information stored in the sorting operation storage region 233cb in order starting from the beginning of the time series. This will be described specifically below.

As described above, the information written in the sorting operation storage region 233cb is the unit sorting information e generated by the X-ray inspection device 220, and is information including N number of numerical values. When the numerical value is "1", the command generating component 233db generates a command to discharge air for the first air sorting mechanism 231a and generates a command to prohibit the discharge of air for the second air sorting mechanism 231b and the third air sorting mechanism 231c. When the numerical value is "2", the command generating component 233db generates a command to discharge air for the second air sorting mechanism 231b and generates a command to prohibit the discharge of air for the first air sorting mechanism 231a and the third air sorting mechanism 231c. When the numerical value is "3", the command generating component 233db generates a command to discharge air for the third air sorting mechanism 231c and generates a command to prohibit the discharge of air for the first air sorting mechanism 231a and the second air sorting mechanism 231b. When the numerical value is "0", the command generating component 233db generates a command to prohibit the discharge of air and sends it to all of the first to third air sorting mechanisms 231a, 231b, and 231c.

It should be noted that the time in which the first to third air sorting mechanisms 231a, 231b, and 231c discharge air or prohibit the discharge of air based on each piece of numerical value information is the time in which the conveyance device 10 conveys the inspection article P a distance given by (width L/N) or in other words a single imaging width u of the line sensor 23. That is to say, the time in which the air sorting mechanism 31 discharges air or prohibits the discharge of air based on each piece of numerical value information is a time obtained by dividing the distance given by (width L/N) by the conveyance speed V of the conveyance device 10. It should be noted that the width L here is, as described above, a predetermined distance along the conveyance direction of the conveyance device 10 for which the control component 224d of the X-ray inspection device 220 generates a set of unit sorting information e. N is the number of numerical values included in the unit sorting information e.

The command for the first air sorting mechanism 231a may be generated by the command generating component 233db in the same way as the command for the air sorting mechanism 31 is generated in the first embodiment. In contrast, the commands for the second air sorting mechanism 231b and the third air sorting mechanism 231c by the command generating component 233db are generated as follows.

The timing when the sorting operation storage rewriting component 233da rewrites the sorting operation storage region 233cb is determined so as to match the timing when the inspection article P passes in front of the first nozzle 232a of the first air sorting mechanism 231a. On the other hand, the second nozzle 232b of the second air sorting mechanism 231b is disposed the distance B1 apart from the first nozzle 232a on the downstream side in the conveyance direction of the conveyance device 10 (see FIG. 7). The third nozzle 232c of the third air sorting mechanism 231c is disposed the distance B2 apart from the first nozzle 232a on the downstream side in the conveyance direction of the conveyance device 10 (see FIG. 7). Consequently, if the operation of the second air sorting mechanism 231b and the third air sorting mechanism 231c is controlled at the timing when the inspection article P passes in front of the first nozzle 232a of the first air sorting mechanism 231a, air cannot be discharged at an appropriate timing. Therefore, the command generating component 233db generates for the second air sorting mechanism 231b a control command to be executed after the elapse of a time calculated by distance B1/conveyance speed V based on the conveyance speed V of the conveyance device 10 sent from the encoder 13 and the distance B1 between the first nozzle 232a and the second nozzle 232b which is stored in the storage component 233c. Also, the command generating component 233db generates for the third air sorting mechanism 231c a control command executed after the elapse of a time calculated by distance B2/conveyance speed V based on the conveyance speed V of the conveyance device 10 sent from the encoder 13 and the distance B2 between the first nozzle 232a and the third nozzle 232c which is stored in the storage component 233c.

(3) Process Executed by Sorting Device

The rewriting processes of the sorting information storage region 233ca and the sorting operation storage region 233cb are the same as the ones in the first embodiment, so here detailed description thereof will be omitted.

(4) Characteristics

The inspection and sorting system 200 has the same characteristics as (4-1) to (4-3) and (4-5) of the inspection and sorting system 100 pertaining to the first embodiment. In addition, the inspection and sorting system 200 pertaining to the second embodiment has the following characteristic.

(4-1)

In the inspection and sorting system 200 pertaining to the above embodiment, the X-ray inspection device 220 can perform a rank inspection based on the weights of the inspection articles P.

Here, the inspection articles P can be sorted based on the ranks of the inspection articles P using the sorting device 230.

Third Embodiment

An inspection and sorting system 300 pertaining to a third embodiment of the present invention will be described.

(1) Overall Configuration

The inspection and sorting system 300 pertaining to the third embodiment, similar to the inspection and sorting system 100 of the first embodiment, sorts the inspection articles P so that non-defective articles not contaminated with foreign matter is conveyed to a downstream process (e.g., a boxing process) and defective articles contaminated with foreign matter is removed from the line based on the results of the foreign matter inspection of inspection articles P. The inspection and sorting system 300 also checks whether the sorting is properly carried out by the sorting device 30.

Figure 10:
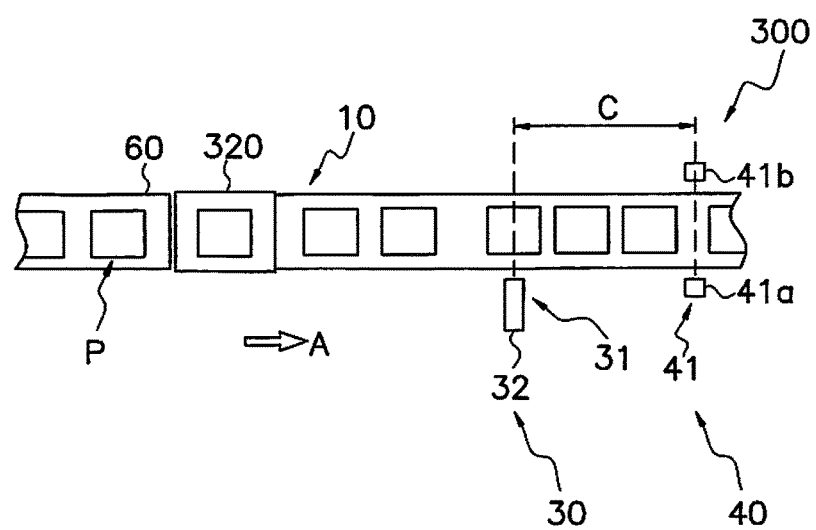
FIG. 10 is a schematic diagram of an inspection and sorting system pertaining to a third embodiment of the present invention.

The inspection and sorting system 300 is mainly provided with the conveyance device 10, an X-ray inspection device 320, the sorting device 30, and a checking device 40 (see FIG. 10).

The conveyance device 10 receives the inspection articles P conveyed thereto by the upstream conveyor unit 60 and conveys the received inspection articles P. The arrow A in FIG. 10 indicates the conveyance direction of the conveyance device 10. The X-ray inspection device 320 performs the foreign matter inspection of the inspection articles P conveyed by the conveyance device 10. The sorting device 30 executes a sorting operation that sorts the inspection articles P conveyed by the conveyance device 10 based on the inspection results of the X-ray inspection device 320. The checking device 40 judges, on the downstream side of the sorting device 30 in the conveyance direction of the conveyance device 10, whether the operation of sorting the inspection articles P has been appropriately executed by the sorting device 30.

The conveyance device 10 and the sorting device 30 are the same as the ones in the first embodiment. The X-ray inspection device 320 differs from the X-ray inspection device 20 in the first embodiment in that the X-ray inspection device 320 is also connected, by a communication line 90 such as the Internet, to the checking device 40 and also sends the sorting information D and the reference signal S, via the communication line 90, to the checking device 40. Furthermore, the X-ray inspection device 320 differs from the one in the first embodiment in that the X-ray inspection device 320 sends both the sorting information D and the reference signal S to the sorting device 30 by the communication line 90 such as the Internet. In other respects, the X-ray inspection device 320 and the X-ray inspection device 20 are the same.

(2) Detailed Configuration

The checking device 40 of the inspection and sorting system 300 will be described below in detail. Description regarding the conveyance device 10, the X-ray inspection device 320, and the sorting device 30 will be omitted.

(2-1) Checking Device

The checking device 40 is a device that checks whether the inspection articles P have been properly sorted by the sorting device 30 based on the results of the foreign matter inspection by the X-ray inspection device 320.

Figure 11:
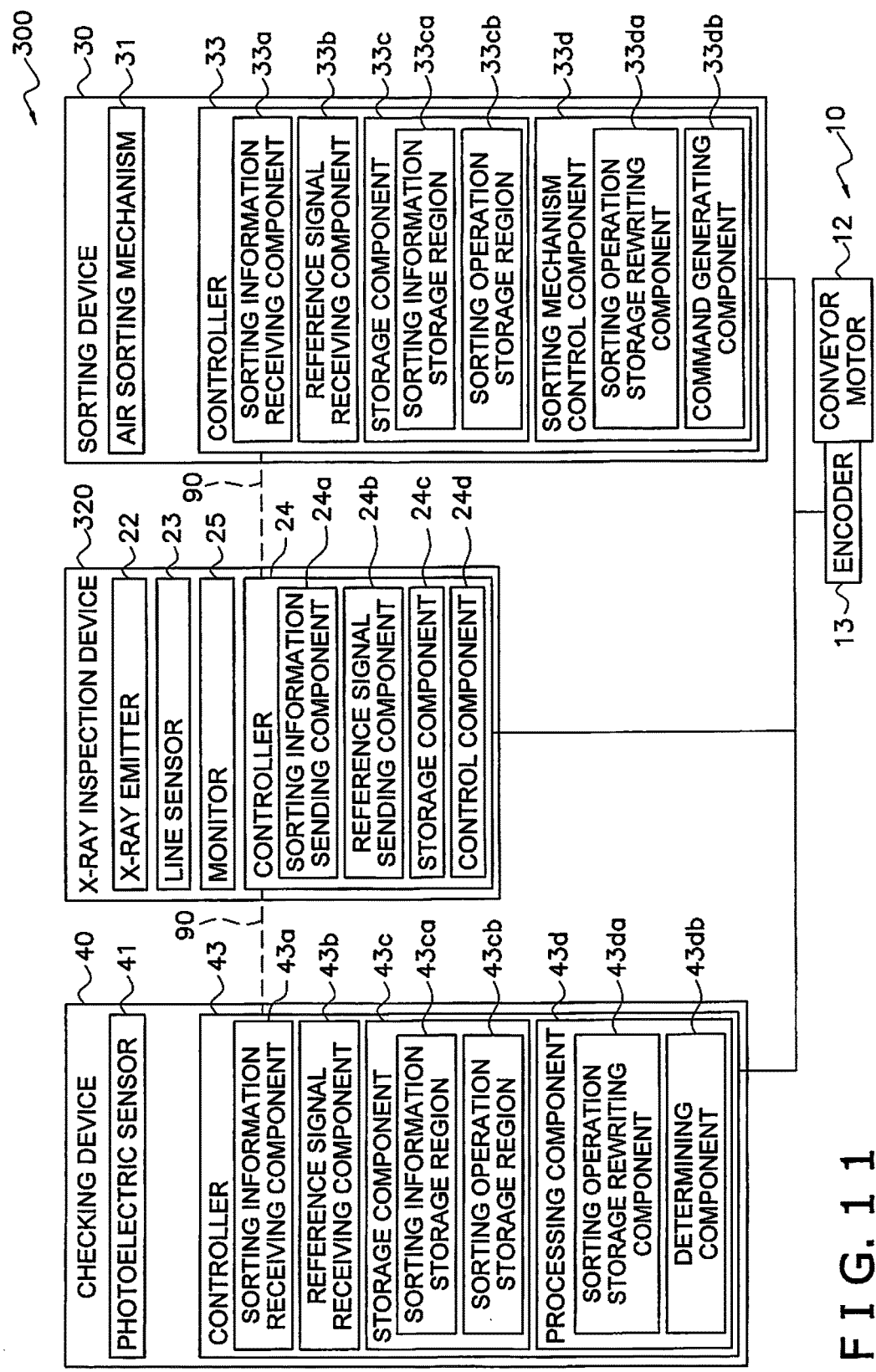
FIG. 11 is a block diagram of the inspection and sorting system of FIG. 10.

The checking device 40 mainly has a photoelectric sensor 41 and a controller 43 (see FIG. 11).

(2-1-1) Photoelectric Sensor

The photoelectric sensor 41 is an example of a conveyance checking sensor that detects the inspection articles P on the downstream side of the nozzle 32 of the air sorting mechanism 31 in the conveyance direction of the conveyance device 10 (see FIG. 10). The photoelectric sensor 41 includes a light emitter 41a and a light receiver 41b that form a pair and are disposed on either side of the conveyor belt 11 (see FIG. 10). Whether or not the photoelectric sensor 41 detects the inspection article P, or in other words whether or not the light receiver 41b detects the light emitted by the light emitter 41a, is continuously sent to the controller 43.

(2-1-2) Controller

The controller 43 is a computer that controls each part of the checking device 40. The controller 43 has a CPU that performs calculation and control, a ROM, a RAM, a hard disk, and the like that serve as storage components that store information.

The controller 43 has a sorting information receiving component 43a and a reference signal receiving component 43b that receive information/signals from the controller 24 of the X-ray inspection device 320 (see FIG. 11). Furthermore, the controller 43 has a storage component 43c and a processing component 43d (see FIG. 11). The processing component 43d mainly has a CPU and executes a program stored in the storage component 43c to thereby judge, based on the detection results of the inspection articles P by the photoelectric sensor 41, the success or failure of the sorting by the sorting device 30. The storage component 43c stores the program executed by the processing component 43d and various types of information. The storage component 43c includes a sorting information storage region 43ca, which stores the sorting information D sent from the X-ray inspection device 320, and a sorting operation storage region 43cb, which is used when the processing component 43d judges the success or failure of the sorting by the sorting device 30 (see FIG. 11). The information stored in the sorting operation storage region 43cb is the aforementioned unit sorting information d.

The controller 43 is electrically connected to the photoelectric sensor 41. Furthermore, the controller 43 is also electrically connected to the encoder 13 of the conveyance device 10 (see FIG. 11). The controller 43 acquires data relating to the rotation speed of the conveyor motor 12 from the encoder 13 and grasps, based on the acquired data, the conveyance distance and conveyance speed of the inspection articles P.

Furthermore, the controller 43 is connected to the controller 24 of the X-ray inspection device 320 by the communication line 90 in order to receive the sorting information D and the reference signal S (see FIG. 11).

(2-1-2-1) Sorting Information Receiving Component

The sorting information receiving component 43a receives the sorting information D, which relates to the sorting of the inspection articles P based on the inspection results of the X-ray inspection device 320 and is sent by the sorting information sending component 24a of the controller 24 of the X-ray inspection device 320. The function of the sorting information receiving component 43a is the same as that of the sorting information receiving component 33a of the sorting device 30. Here, detailed description regarding the sorting information receiving component 43a will be omitted.

(2-1-2-2) Reference Signal Receiving Component

The reference signal receiving component 43b receives the fixed-interval reference signal S relating to the conveyance by the conveyance device 10. The function of the reference signal receiving component 43b is the same as that of the reference signal receiving component 33b of the sorting device 30. Here, detailed description regarding the reference signal receiving component 43b will be omitted.

(2-1-2-3) Storage Component (2-1-2-3-1) Sorting Information Storage Region

The sorting information D received by the sorting information receiving component 43a is stored in the sorting information storage region 43ca. The function of the sorting information storage region 43ca is the same as that of the sorting information storage region 33ca of the sorting device 30. Here, detailed description regarding the sorting information storage region 43ca will be omitted.

(2-1-2-3-2) Sorting Operation Storage Region

The set of unit sorting information d furthest downstream in the conveyance direction of the conveyance device 10, or in other words the oldest N bits of information in terms of the time series, in the sorting information D stored in the sorting information storage region 43*ca* is written to the sorting operation storage region 43*cb* by a sorting operation storage rewriting component 43*da* of the processing component 43*d* described later and stored in the sorting operation storage region 43*cb*. The content of the sorting operation storage region 43*cb* is rewritten at a timing adjusted by the reference signal S received by the reference signal receiving component 43*b*.

(2-1-2-4) Processing Component

The processing component 43*d* judges the success or failure of the sorting by the air sorting mechanism 31 based on the sorting information D received by the sorting information receiving component 43*a* and in accordance with whether or not the photoelectric sensor 41 detects the inspection articles P at the timing adjusted by the reference signal S received by the reference signal receiving component 43*b*. The processing component 43*d* is an example of a judging component.

The processing component 43*d* mainly has, as sub-function components, a sorting operation storage rewriting component 43*da* and a determining component 43*db* (see FIG. 11).

(2-1-2-4-1) Sorting Operation Storage Rewriting Component

The sorting operation storage rewriting component 43*da* rewrites the content stored in the sorting operation storage region 43*cb* based on the sorting information D stored in the sorting information storage region 43*ca* and at the timing adjusted by the reference signal S received by the reference signal receiving component 43*b*. As described later, when the content of the sorting operation storage region 43*cb* is rewritten, the determining component 43*db* starts, using that timing, the judging based on the rewritten content. Therefore, the timing of the rewriting of the content of the sorting operation storage region 43*cb* determines the timing of the determination by the determining component 43*db*.

The timing when the sorting operation storage rewriting component 43*da* rewrites the information in the sorting operation storage region 43*cb* will be described in detail.

The sorting information D is, as described above, information for controlling the air sorting mechanism 31 so that in a case where it is supposed that the air sorting mechanism 31 could operate without delay when it receives a command to operate, air would be discharged from the nozzle 32 when the inspection article P to be sorted passes a point located before the actual position of the nozzle 32 by the delay adjustment width α when controlling the air sorting mechanism 31 based on the sorting information D. However, the photoelectric sensor 41 of the checking device 40 is installed a predetermined distance C away on the downstream side of the position of the nozzle 32 in the conveyance direction of the conveyance device 10 (see FIG. 10). Furthermore, as the photoelectric sensor 41 detects the presence or absence of the inspection articles P using light, virtually no detection delay arises. For that reason, if the sorting operation storage rewriting component 43*da* rewrites the information in the sorting operation storage region 43*cb* at the same time as the rise or fall of the reference signal S, the detection result of the photoelectric sensor 41 is compared with inappropriate information by the later-described determining component 43*db* without being compared with the content of the sorting operation storage region 43*cb* that should be compared with the content of the detection result.

Therefore, considering the delay adjustment width α and the distance C between the nozzle 32 and the photoelectric sensor 41, the sorting operation storage rewriting component 43*da* writes to the sorting operation storage region 43*ca* a set of unit sorting information d furthest downstream in the conveyance direction of the conveyance device 10 in the sorting information D stored, at the point in time of the detection of the rise or fall of the reference signal S, in the sorting information storage region 43*ca*, after a time calculated by (delay adjustment width α+distance C)/conveyance speed V from the rise or fall of the reference signal S.

(2-1-2-4-2) Determining Component

The determining component 43*db* determines, based on the content stored in the sorting operation storage region 43*cb* and the detection result of the photoelectric sensor 41 which is sent in real time, whether the inspection article P that should have been sorted by the sorting device 30 is being conveyed by the conveyor belt 11. Specifically, when the content of the sorting operation storage region 43*cb* is rewritten, the determining component 43*db* starts, at that timing, a comparison between the content of the sorting operation storage region 43*cb* and the detection result of the photoelectric sensor 41 which is sent in real time, in order to check whether the sorting operation according to the time series information stored in the sorting operation storage region 43*cb* was executed or not by the air sorting mechanism 31. This will be specifically described below.

As described above, the information written in the sorting operation storage region 43*cb* is the unit sorting information d generated by the X-ray inspection device 320, and is N bits of binary information. When the value of the bit is "1", the determining component 43*db* determines whether the light receiver 41*b* of the photoelectric sensor 41 is receiving the light at a timing corresponding to that bit. When the light receiver 41*b* is receiving the light (when there is no inspection article P), the determining component 43*db* determines that the sorting was properly executed by the air sorting mechanism 31. On the other hand, when the light receiver 41*b* is not receiving the light (when there is an inspection article P), the determining component 43*db* determines that the sorting was not properly executed by the air sorting mechanism 31.

It should be noted that the time during which the determining component 43*db* performs the determination based on each bit of information is the time in which the conveyance device 10 conveys the inspection article P a distance given by (width L/N) or in other words a single imaging width u of the line sensor 23. That is to say, the time in which the determining component 43*db* performs the determination based on each bit of information is a time obtained by dividing the distance given by (width L/N) by the conveyance speed V of the conveyance device 10. It should be noted that the width L here is, as described above, a predetermined distance along the conveyance direction of the conveyance device 10 for which the control component 24*d* of the X-ray inspection device 320 generates a unit sorting information d. N is the number of bits of the unit sorting information d.

(3) Process Executed by Sorting Device

The process executed by the sorting device 30 is the same as the one in the first embodiment, so here detailed description thereof will be omitted.

(4) Process Executed by Checking Device

Figure 12:
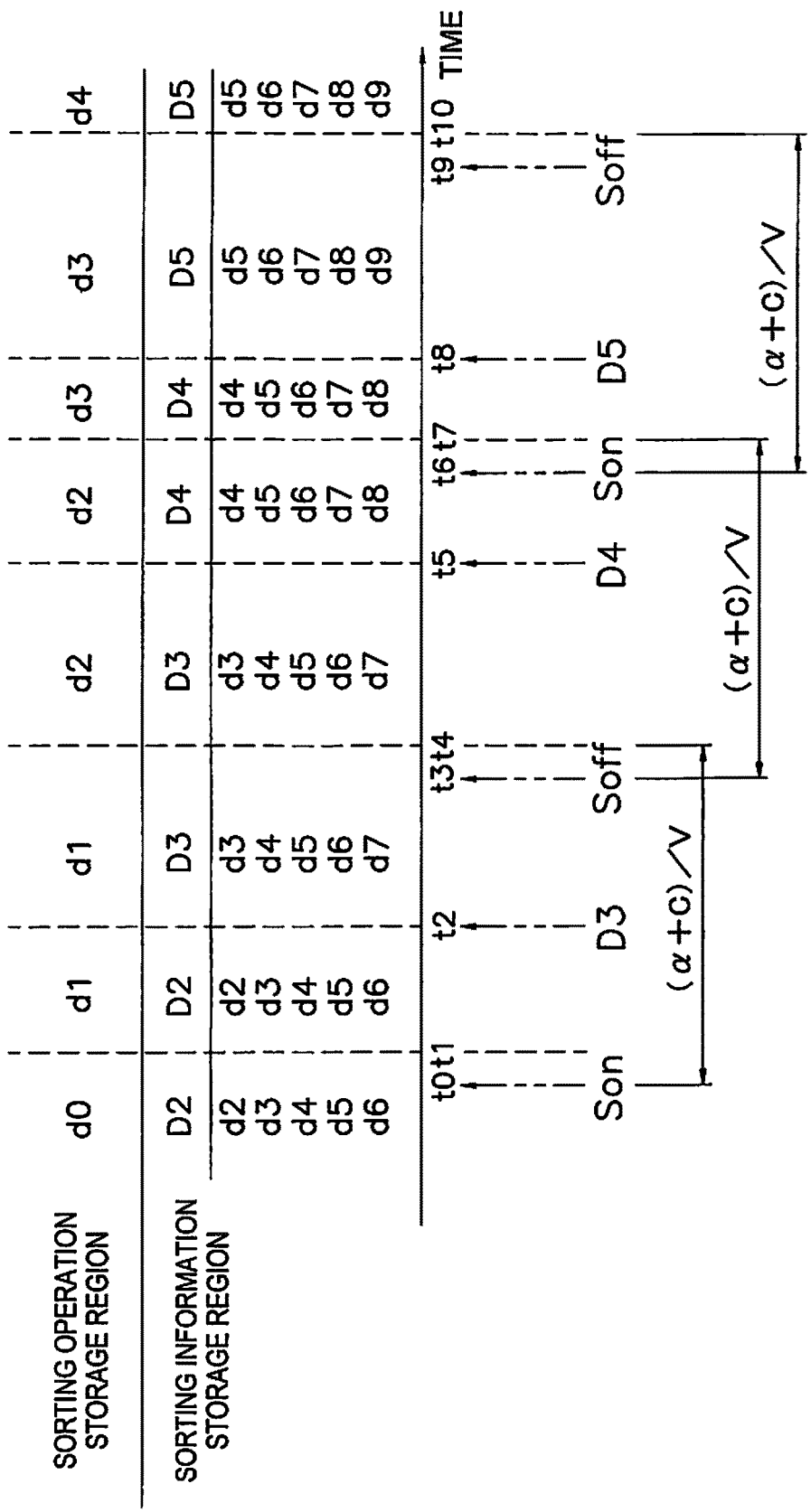
FIG. 12 is a drawing for describing the timing of a process of rewriting a sorting operation storage region and a sorting information storage region in a checking device of the inspection and sorting system of FIG. 10.

The process executed by the checking device 40, and particularly the process of rewriting the sorting information storage region 43*ca* and the sorting operation storage region 43*cb*, will be described using FIG. 12.

First, as a premise, it is supposed that at a given time (point in time t0 in FIG. 12) the sorting information D2 including the sets of unit sorting information d2 to d6 is stored in the sorting information storage region 43*ca*. It should be noted that the smaller the numbers added to the sets of unit sorting information d2 to d6 are, the further downstream the information is in the conveyance direction of the conveyance device 10 (in other words, the older the information is). Furthermore, it is supposed that at the point in time t0 in FIG. 12 the sorting mechanism control component 33*d* detects the rise of the reference signal S (expressed as Son in FIG. 12) received by the reference signal receiving component 43*b*. It should be noted that, here, it is supposed that the conveyance speed of the conveyance device 10 is fixed at the conveyance speed V.

In this case, the sorting operation storage rewriting component 43*da* rewrites the content of the sorting operation storage region 43*cb* from the unit sorting information that has been stored until then to the oldest set of unit sorting information d2 in the sorting information D2 that had been stored, at the point in time t0 (the point in time of the detection of the rise of the reference signal S), in the sorting information storage region 43*ca* at time t4 after the elapse of a time calculated by {(delay adjustment width α+distance C)/conveyance speed V} from the point in time t0 when the rise of the reference signal S was detected. When the content of the sorting operation storage region 43*cb* is rewritten, the determining component 43*db* judges the success or failure of the sorting of the inspection articles P in accordance with the newly rewritten unit sorting information d2 at the timing of the rewriting of the sorting operation storage region 43*cb*.

Furthermore, it is supposed that at a given time t2 the sorting information receiving component 43*a* receives sorting information D3 including sets of unit sorting information d3 to d7. At this time, the content of the sorting information storage region 43*ca* is rewritten from the sorting information D2 to the newly received sorting information D3. At this time, the content of the sorting operation storage region 43*cb* is not changed. In this way, the timing of the reception of the sorting information D does not affect the timing of the rewriting of the sorting operation storage region 43*cb*. Therefore, even if the timing of the reception of the sorting information D varies, this does not affect the timing when the checking device 40 checks the success or failure of the sorting of the inspection articles P.

Next, when at a given time t3 the fall of the reference signal S (expressed as Soff in FIG. 12) received by the reference signal receiving component 43*b* is detected, at time t7 after the elapse of a time calculated by {(delay adjustment width α+distance C)/conveyance speed V} from the time t3, the content of the sorting operation storage region 43*cb* is rewritten from the unit sorting information d2 that has been stored until then to the oldest set of unit sorting information d3 in the sorting information D3 that is stored in the sorting information storage region 43*ca* at the point in time t3 (the point in time of the detection of the fall of the reference signal S). When the content of the sorting operation storage region 43*cb* is rewritten, the determining component 43*db* judges the success or failure of the sorting of the inspection articles P in accordance with the newly rewritten unit sorting information d3 at the timing of the rewriting of the sorting information storage region 43*cb*.

As what follows thereafter is similar description thereof will be omitted.

The checking device 40 executes a predetermined operation when the processing component 43*d* judges that the sorting by the air sorting mechanism 31 has failed. The predetermined operation is, for example, a notification of the failure of the sorting to the operator and/or the transmission of a signal for stopping the operation of the inspection and sorting system 300.

(5) Characteristics

The inspection and sorting system 300 has the same characteristics as those of the inspection and sorting system 100 pertaining to the first embodiment.

Another characteristic of the inspection and sorting system 300 pertaining to the third embodiment is described below.

(5-1)

The inspection and sorting system 300 pertaining to the third embodiment is provided with the photoelectric sensor 41 serving as an example of a conveyance checking sensor and the processing component 43*d* serving as an example of a judging component. The photoelectric sensor 41 detects the inspection articles P on the downstream side of the air sorting mechanism 31 in the conveyance direction of the conveyance device 10. The processing component 43*d* judges, based on the detection result of the photoelectric sensor 41, the success or failure of the sorting by the air sorting mechanism 31. The processing component 43*d* judges the success or failure of the sorting by the air sorting mechanism 31 based on the sorting information D and in accordance with whether or not the photoelectric sensor 41 detects the inspection articles P at a check timing adjusted by the reference signal S.

Here, the photoelectric sensor 41 which detects the inspection articles P conveyed on the downstream side of the air sorting mechanism 31 is installed, and the success or failure of the sorting is judged based on the sorting information D and in accordance with whether or not an inspection article P is detected at the check timing adjusted by the reference signal S. That is to say, here, the presence or absence of an inspection article P is judged at an accurate check timing adjusted by the reference signal S in the same way as the timing of the operation of the air sorting mechanism 31, and the success or failure of the sorting is thereby judged. For that reason, the success or failure of the sorting can be judged at a high processing speed and accurately.

MODIFICATIONS

The first to third embodiment may be combined with each other to the extent that they do not contradict each other. For example, the inspection and sorting system may be provided with both the sorting device 30 of the first embodiment and the sorting device 230 of the second embodiment, and the sorting of the inspection articles P may be performed in accordance with the non-defective/defective of the inspection articles P and the rank of the inspection articles P based on the results of the foreign matter inspection and the rank inspection performed by the X-ray inspection device 20.

Modifications of the embodiments will be described below. It should be noted that plural modifications may also be appropriately combined.

(1) Modification A

In the above embodiments, the sorting devices 30 and 230 have the sorting operation storage regions 33*cb* and 233*cb* and adjust, with the reference signal S, the timing when the sorting operation storage rewriting components 33da and 233da perform the rewriting, but the sorting devices 30 and 230 are not limited to this.

For example, the sorting devices 30 and 230 may not have the sorting operation storage regions 33cb and 233cb, and the command generating components 33db and 233db may directly reference the sorting information storage regions 33ca and 233ca to generate the commands that control the air sorting mechanisms 31, 231a, 231b, and 231c. And, the air sorting mechanisms 31, 231a, 231b, and 231c may be made to perform the same operations as in the above embodiments by changing the reference positions in the sorting information storage regions 33ca and 233ca (the positions referenced by a pointer) at the timing adjusted by the reference signal S.

It is similar for the checking device 40.

(2) Modification B

In the above embodiments, the sorting devices 30 and 230 execute the sorting of the inspection articles P with air discharged from the air sorting mechanisms 31, 231a, 231b, and 231c, but the sorting mechanism is not limited to this kind of a mechanism that sorts the inspection articles P by discharging air. For example, the sorting mechanism may be a mechanism that sorts the inspection articles P by driving an arm driven by a motor or an air cylinder.

(3) Modification C

In the above embodiments, the inspection device is the X-ray inspection devices 20 and 220, but the inspection device is not limited to this. For example, the inspection device may be a near-infrared inspection device that inspects the non-defective/defective of the inspection articles P by detecting near-infrared radiation transmitted through the inspection articles P and performing an inspection of the sealing of seal portions or the like, or a metal detection device detecting metal contamination in the inspection articles P by using the detection results of a magnetic field.

(4) Modification D

In the third embodiment, the sorting device 30 and the checking device 40 are separate devices, but the embodiment is not limited to this. The controller 33 of the sorting device 30 may be configured to judge the success or failure of the sorting by the air sorting mechanism 31 based on the detection results of the photoelectric sensor 41.

(5) Modification E

In the above embodiments, the X-ray inspection devices 20 and 220 send the reference signal S, but the inspection and sorting system is not limited to this. For example, the inspection and sorting system may also be configured so that, instead of the X-ray inspection devices 20 and 220 sending the reference signal S, the conveyance device 10 sends a signal that is the same as the reference signal S.

(6) Modification F

In the above embodiments, the reference signal S is a signal that is switched on or off each time the conveyance distance of the conveyance device 10 becomes equal to the width L, but the reference signal S is not limited to this.

For example, the reference signal S may be a signal that is switched on or off each time the conveyance distance of the conveyance device 10 becomes a distance equal to half the width L. In this case, the timing of the sorting operation of the air sorting mechanisms 31, 231a, 231b, and 231c may be adjusted based on either one of the rise or fall of the reference signal S.

(7) Modification G

In the above embodiments, the air sorting mechanisms 31, 231a, 231b, and 231c are controlled to always discharge air while the inspection article P to be sorted passes in front of the nozzles 32, 232a, 232b, and 232c, but the inspection and sorting system is not limited to this. It is sufficient if the unit sorting information d and e which determines the sorting operation of the air sorting mechanisms 31, 231a, 231b, and 231c has a content with which the inspection articles P to be sorted can be sorted with the sorting operation executed by the air sorting mechanisms 31, 231a, 231b, and 231c.

(8) Modification H

In the above embodiments, the discharge/stopping of the air by the air sorting mechanisms 31, 231a, 231b, and 231c is switched each time the conveyance distance of the conveyance device 10 becomes equal to the imaging width u of the line sensor 23 at the shortest case, but it is not limited to this. For example, the discharge/stopping of the air by the air sorting mechanisms 31, 231a, 231b, and 231c may be controlled so as to not be switched unless the conveyance distance of the conveyance device 10 becomes equal to an integral multiple (e.g., three times) of the imaging width u of the line sensor 23 at the shortest.

(9) Modification I

In the above embodiments, the reference signal S is a signal transmitted to the reference signal receiving component 33b each time the conveyance device 10 conveys a predetermined distance, but it is not limited to this. For example, in a case where the conveyance speed of the conveyance device 10 is fixed, the fixed-interval reference signal relating to the conveyance by the conveyance device 10 may be a signal transmitted at a fixed time interval.

(10) Modification J

In the above embodiments, the sorting device 30 removes, with air, the inspection articles P from the conveyor belt 11 of the conveyance device 10, but it is not limited to this. For example, instead of removing the inspection articles P from the conveyor belt 11, the sorting device may execute a sorting operation that sorts the inspection articles P by driving a marking mechanism or the like based on the non-defective/defective of the inspection articles P and thereby marking on the inspection articles P (e.g., by marking only defective articles).

INDUSTRIAL APPLICABILITY

The present invention is useful as an inspection and sorting system that can sort articles conveyed by a sorting mechanism based on the inspection results at a high processing speed and with good precision.

What is claimed is:

1. An inspection and sorting system comprising:
   a conveying device configured to convey articles;
   an inspection device configured to inspect the articles conveyed by the conveying device;
   a sorting device having a sorting mechanism being configured to execute a sorting operation in which the articles conveyed by the conveying device are sorted, and
   a reference signal sending component configured to send a fixed-interval reference signal each time the conveying device conveys a predetermined distance, the reference signal being sent independently from an inspection process of the inspection device,
   wherein the sorting device has
      a first receiving component configured to receive sorting information relating to the sorting of the articles based on an inspection result of the inspection device;

a second receiving component configured to receive the reference signal relating to the conveyance by the conveying device; and a sorting mechanism control component configured to control the sorting mechanism to execute the sorting operation based on the sorting information at a timing determined by a receiving timing of the reference signal.

2. The inspection and sorting system according to claim 1, wherein the inspection device is an X-ray inspection device having a line sensor, the line sensor is configured to image, in every single imaging, a predetermined width along a conveyance direction of the conveyance device, and the first distance is an integral multiple of the predetermined width.

3. The inspection and sorting system according to claim 2, wherein the inspection device is configured to inspect the non-defective/defective or rank of the articles.

4. The inspection and sorting system according to claim 3, further comprising a conveyance checking sensor configured to detect the articles on the downstream side of the sorting mechanism in a conveyance direction of the conveying device; and a judging component configured to judge, based on the detection results of the conveyance checking sensor, the success or failure of the sorting by the sorting mechanism, wherein the judging component is configured to judge the success or failure of the sorting by the sorting mechanism based on the sorting information and in accordance with whether or not the conveyance checking sensor detects the articles at a check timing adjusted by the reference signal.

5. The inspection and sorting system according to claim 4, wherein the timing is determined based on a fixed delay time determined by a characteristic of the sorting mechanism.

6. The inspection and sorting system according to claim 1, wherein the inspection device is configured to inspect the non-defective/defective or rank of the articles.

7. The inspection and sorting system according to claim 1, further comprising a conveyance checking sensor configured to detect the articles on the downstream side of the sorting mechanism in a conveyance direction of the conveying device; and a judging component configured to judge, based on the detection results of the conveyance checking sensor, the success or failure of the sorting by the sorting mechanism, wherein the judging component is configured to judge the success or failure of the sorting by the sorting mechanism based on the sorting information and in accordance with whether or not the conveyance checking sensor detects the articles at a check timing adjusted by the reference signal.

8. The inspection and sorting system according to claim 2, further comprising a conveyance checking sensor configured to detect the articles on the downstream side of the sorting mechanism in a conveyance direction of the conveying device; and a judging component configured to judge, based on the detection results of the conveyance checking sensor, the success or failure of the sorting by the sorting mechanism, wherein the judging component is configured to judge the success or failure of the sorting by the sorting mechanism based on the sorting information and in accordance with whether or not the conveyance checking sensor detects the articles at a check timing adjusted by the reference signal.

9. The inspection and sorting system according to claim 1, wherein the timing is determined based on a fixed delay time determined by a characteristic of the sorting mechanism.

10. The inspection and sorting system according to claim 2, wherein the timing is determined based on a fixed delay time determined by a characteristic of the sorting mechanism.

11. The inspection and sorting system according to claim 3, wherein the timing is determined based on a fixed delay time determined by a characteristic of the sorting mechanism.

* * * * *